(12) United States Patent
Federici

(10) Patent No.: US 9,389,172 B2
(45) Date of Patent: Jul. 12, 2016

(54) METHODS AND APPARATUS FOR THE NON-DESTRUCTIVE MEASUREMENT OF DIFFUSION IN NON-UNIFORM SUBSTRATES

(75) Inventor: John F. Federici, Westfield, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 370 days.

(21) Appl. No.: 13/284,244

(22) Filed: Oct. 28, 2011

(65) Prior Publication Data

US 2012/0037804 A1     Feb. 16, 2012

Related U.S. Application Data

(63) Continuation-in-part of application No. 13/024,406, filed on Feb. 10, 2011, now Pat. No. 8,237,452, which is a continuation of application No. 11/965,045, filed on Dec. 27, 2007, now Pat. No. 7,906,975.

(60) Provisional application No. 61/408,408, filed on Oct. 29, 2010, provisional application No. 60/898,208, filed on Jan. 30, 2007.

(51) Int. Cl.
| | |
|---|---|
| *G01N 21/3586* | (2014.01) |
| *G01N 21/47* | (2006.01) |
| *G01N 21/90* | (2006.01) |
| *G01N 33/14* | (2006.01) |
| *G01N 21/3577* | (2014.01) |
| *G01N 21/94* | (2006.01) |
| *G01N 21/95* | (2006.01) |

(52) U.S. Cl.
CPC ........ *G01N 21/3586* (2013.01); *G01N 21/3577* (2013.01); *G01N 21/4795* (2013.01); *G01N 21/909* (2013.01); *G01N 33/146* (2013.01); *G01N 21/94* (2013.01); *G01N 21/95* (2013.01)

(58) Field of Classification Search
CPC ... G01N 21/3586; G01N 21/35; G01N 21/31; G01N 21/4795; G01N 21/94; G01N 21/95; G01N 33/146
USPC ....................................................... 324/639
See application file for complete search history.

(56) References Cited

U.S. PATENT DOCUMENTS

| | | | |
|---|---|---|---|
| 5,038,039 | A | 8/1991 | Wong |
| 5,710,430 | A | 1/1998 | Nuss |
| 6,341,521 | B1 | 1/2002 | Bartolomey |
| 6,479,822 | B1 | 11/2002 | Nelson |
| 6,717,428 | B1 | 4/2004 | Spica |

(Continued)

FOREIGN PATENT DOCUMENTS

WO        0148457 A1     7/2001

OTHER PUBLICATIONS

M. Koch et al., "THz-imaging: A New Method for Density Mapping of Wood" Wood Science and Technology, vol. 32, No. 6, Dec. 1, 1998.

(Continued)

*Primary Examiner* — Jeff Natalini
(74) *Attorney, Agent, or Firm* — Timothy X. Gibson, Esq.; Gibson & Dernier LLP

(57) ABSTRACT

Non-invasive THz spectroscopic apparatus and methods are provided for measuring the average diffusion coefficients for a structure such as cork. The methods may be used to image the localized presence of water in the structure to produce time-dependent images of liquid propagation in the structure.

12 Claims, 16 Drawing Sheets

(56) References Cited

U.S. PATENT DOCUMENTS

| | | | |
|---|---|---|---|
| 7,012,427 B2 | 3/2006 | Augustine | |
| 7,624,344 B2 * | 11/2009 | Mindrum | G06Q 10/10 715/716 |
| 2002/0067480 A1 | 6/2002 | Takahashi | |
| 2004/0010196 A1 | 1/2004 | Wang | |
| 2004/0223214 A1 * | 11/2004 | Atkinson | G02B 21/002 359/385 |
| 2004/0232052 A1 | 11/2004 | Call et al. | |
| 2006/0049356 A1 | 3/2006 | Shen et al. | |
| 2007/0282206 A1 * | 12/2007 | Arnone et al. | 600/473 |
| 2008/0023633 A1 | 1/2008 | Mittleman et al. | |
| 2008/0046189 A1 | 2/2008 | Allende-Blanco et al. | |
| 2008/0165364 A1 * | 7/2008 | Zhao et al. | 356/451 |
| 2008/0180111 A1 | 7/2008 | Federici et al. | |

OTHER PUBLICATIONS

Takeshi Yasui, "Sensitive Measurement of Water Content in Dry Material Based on Low-Frequency Terahertz Time-Domain Spectroscopy" Proceedings of SPIE, vol. 6024, pp. 60240A-60240A-6, Jan. 1, 2006.

Watanabe Y, et al., "Component Analysis of Chemical Mixtures using Terahertz Spectroscopic Imaging" Optics Communications, North-Holland Publishing Co. vol. 234, No. 1-6,pp. 125-129, Apr. 15, 2004.

Yew Li Hor et al., "Nondestructive Evaluation of Cork Enclosures Using Terahertz/Millimeter Wave Spectroscopy and Imaging" Applied Optics, Optical Society of America vol. 47, No. 1, pp. 72-78, Jan. 1, 2008.

Yew Li Hor et al., Terahertz Study of Trichloranisole by Time-Domain Spectroscopy Laser Science, p. 1 Sep. 16, 2007.

Supplementary European Search Report for application EP07869976, dated Oct. 19, 2011.

International Search Report and Written Opinion for PCT application PCT/US2007/088932, Jul. 1, 2008(Form PCT/ISA/237).

Chang, J., et al.: "Cork quality classification system using a unified image processing and fuzzy-neural network methodology," IEEE Transactions on Neural Networks, vol. 8, No. 4, Jul. 1997, pp. 964-974.

Juanola, R., et al.: "Evaluation of an extraction method in the determination of the 2,4,6-trichloroanisole content of tainted cork," Journal of Chromatography A, 953 (2002) 207-214.

Lizarraga, E., et al.: "Determination of chloroanisole compounds in red wine by headspace solid-phase microextraction and gas chromatography-mass spectrometry," Journal of Chromatography A, 1052 (2004) 145-149.

Brunetti, A., et al.: "Cork quality estimation by using Compton tomography," Nuclear Instruments and Methods in Physics Research B 1996 (2002) 161-168.

Zimdars, D., et al.: "Time domain terahertz detection of flaws within space shuttle sprayed on foam insulation," 2004 OSA/CLEO 2004.

Chua, H.S., et al.: "Terahertz time-domain spectroscopy of wheat grain," Spectroscopy and material properties, 2004 IEEE, pp. 399-400.

Chua, H.S., et al.: "Terahertz time-domain spectroscopy of crushed wheat grain," 2005 IEEE, pp. 2103-2106.

Hadjiloucas, S., et al.: "Measurements of leaf water content using terahertz radiation," IEEE Transactions on Microwave Theory and Techniques, vol. 47, No. 2, Feb. 1999, pp. 142-149.

Hadjiloucas, S., et al.: "Analysis of spectroscopic measurements of leaf water content at terahertz frequencies using linear transforms," vol. 19, No. 12/Dec. 2002/J. Opt. Soc. Am. A, pp. 2495-2509.

Reid, M., et al.: "Terahertz birefringence and attenuation properties of wood and paper," Applied Optics, vol. 45, No. 12, Apr. 20, 2006, pp. 2766-2772.

Strachan, C.J., et al., "Using terahertz pulsed spectroscopy to study crystallinity of pharmaceutical materials," Chemical Physics Letters 390, (2004) pp. 20-24.

Venables, D.S., et al.: "Spectroscopy and dynamics of mixtures of water with acetone, acetonitrile, and methanol," Journal of Chemical Physics, vol. 113, No. 24, Dec. 22, 2000, pp. 11222-11236.

Federici, J.F., et al.: THz imaging and sensing for security applications—explosives, weapons and drugs, Semicond. Sci. Technol. 20 (2005) S266-S280.

Beard, M.G., et al.: "Terahertz Spectroscopy," J. Phys. Chem. B 2002, 106, 7146-7159.

Huang, F., et al.: "Terahertz study of 1,3,5-trinitro-s-triazine by time-domain and Fourier transform infrared spectroscopy," Applied Physics Letters, vol. 85, No. 23, Dec. 6, 2004, pp. 5535-5537.

Karlsson, S., et al.: "Formation of 2,4,6-trichlorophenol and 2,4,6-trichloroanisole during treatment and distribution of drinking water," Wat. Sci. Tech., vol. 31, No. 11, pp. 99-103, 1995.

Prescott, J., et al.: "Estimating a "consumer rejection threshold" for cork taint in white wine," Food Quality and Preference 16 (2005) 345-349.

Miki, A., et al.: "Identification of 2,4,6-trichloroanisole (TCA) causing a musty/muddy off-flavor in sake and its production of rice koji and moromi mash," Journal of Bioscience and Bioengineering, vol. 100, No. 2, 178-183, 2005.

Aung, L.H., et al.: "Investigations into the origin of chloroanisoles causing musty off-flavor of raisins," J. Agric. Food Chem. 1996, 44, 3294-3296.

Mittleman, D.M., et al.: "T-ray tomography," Optics Letters, vol. 22, No. 12, Jun. 15, 1997, pp. 904-906.

Yasuda, T., et al.: "Real-time two-dimensional terahertz tomography of moving objects," Optics Communications 267 (2006) 128-136.

Zhong, H., et al.: "Nondestructive defect identification with terahertz time-of-flight tomography," IEEE Sensors Journal, vol. 5, No. 2, Apr. 2005, pp. 203-208.

E. Herve, S. Price, G. Burns, P. Weber, presented at the ASEV Annual Meeting, Reno, Nevada, Jul. 2, 1999. http://www.corkqc.com/asev/asev2-2.htm.

D. Zimdars, J.S. White, G. Stuk, A. Chernovsky, G. Fichter, and S. Williamson, "Large area terahertz imaging and non-destructive evaluation applications," Insight-Non-Destructive Testing and Condition Monitoring 48, 537-539 (2006).

J. F. Federici, D. Gary, R. Barat, Z.-H. Michalopoulou, 'Detection of Explosives by Terahertz Imaging', in Counter-Terrorism Detection Techniques of Explosives Jehuda Yinon Ed. (Elsevier, 2007).

F. C. Delucia, "Spectroscopy in the Terahertz Spectral Region", in Sensing with Terahertz Radiation, D. Mittleman Ed. (Springer, 2003).

A. Nystrom, A. Grimvall, C. Krantz-Rulcker, R. Savenhed, K. Akerstrand, "Drinking water off-flavour caused by 2,4,6-trichloroanisole," Water Science and Technology 25, No. 2, 241-49 (1992).

C. Silva Pereira, J.J. Figueiredo Marques, M.V. San Romao, "Cork taint in wine: Scientific knowledge and public perception—A critical review," Critical Reviews in Microbiology 26(3), 147-62 (2000).

A.P. Pollnitz, K.H. Pardon, D. Liacopoulos, G.K. Skouroumounis, M.A. Sefton, "The analysis of 2,4,6-trichloroanisole and other chloroanisoles in tainted wines and corks," Australian J. Grape and Wine Research 2, 184-90 (1996).

J. Gunschera, F. Fuhrmann, T. Salthammer, A. Schulze, E. Uhde, "Formation and emission of chloroanisoles as indoor pollutants," Environmental Science and Pollution Research 11(3), 147-51 (2004).

D. Mittleman, "Terahertz Imaging" in Sensing with Terahertz Radiation, D. Mittleman Ed. (Springer, 2003).

International Preliminary Report on Patentability for PCT application PCT/US2007/088932, Aug. 4, 2009 (Form PCT/IB/326/373/PCT/ISA/237).

Office Action for U.S. Appl. No. 11/965,045, dated Dec. 10, 2009.

Office Action for U.S. Appl. No. 11/965,045, dated Jul. 19, 2010.

International Search Report and Written Opinion for corresponding application PCT/US11/58333, PCT/ISA/220/210/237, dated Mar. 6, 2012.

Nielsen et al., "Fast Fluid Registration of Medical Images" in Visualization in Biomedical Computing: Lecture Notes in Computer Science, vol. 1131/1996, p. 265-276, 1996.

International Preliminary Report on Patentability and Written Opinion for corresponding application PCT/US11/58333, PCT/ISA/220/210/237, dated Apr. 30, 2013.

* cited by examiner

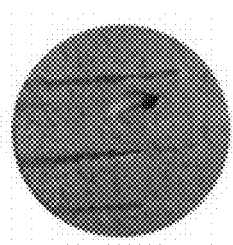 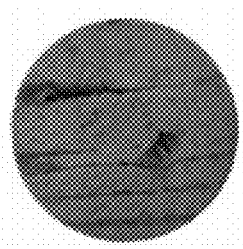 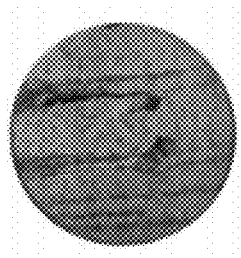
FIG. 11A  FIG. 11B  FIG 11C
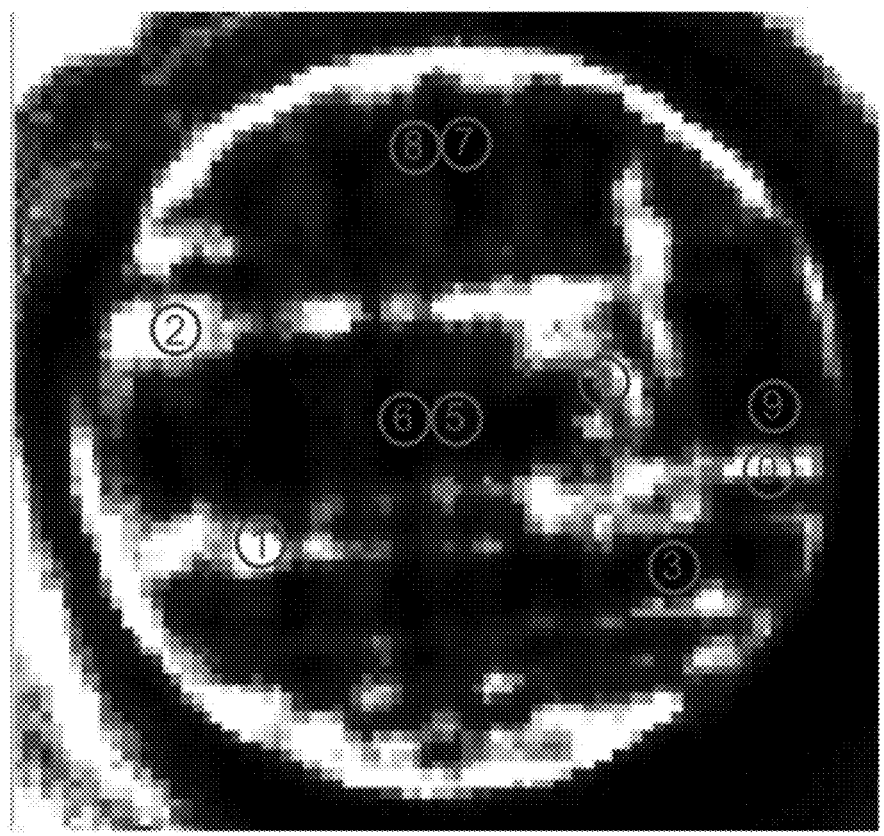
FIG. 12

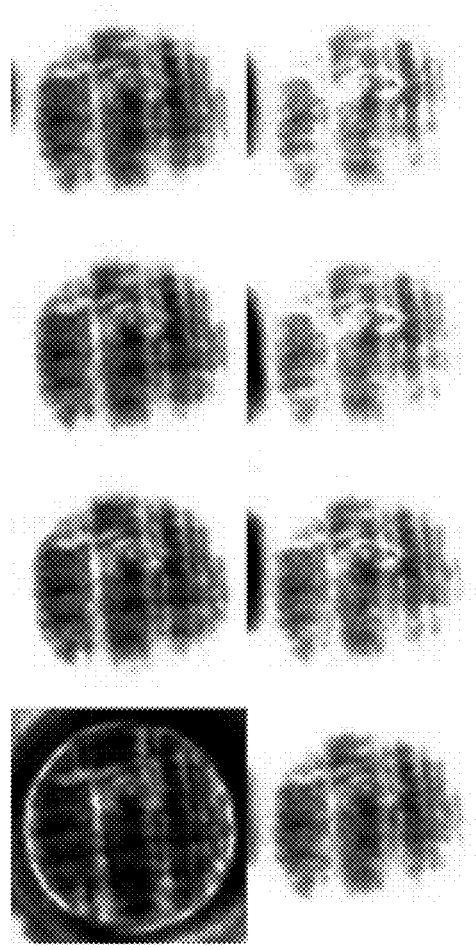

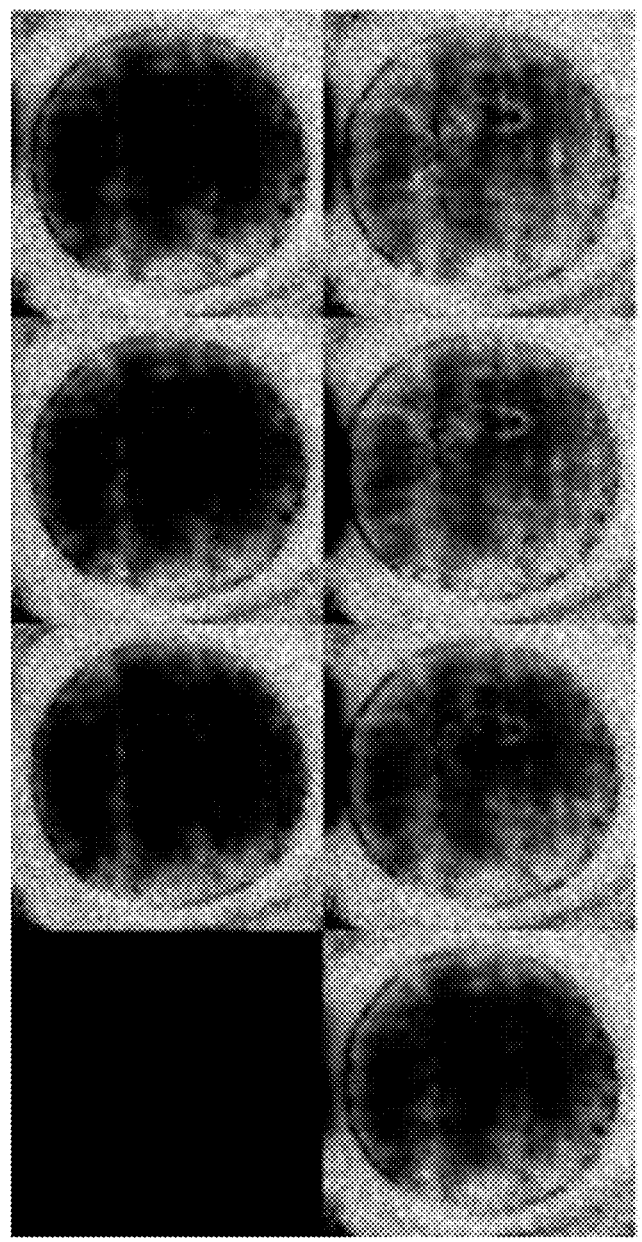

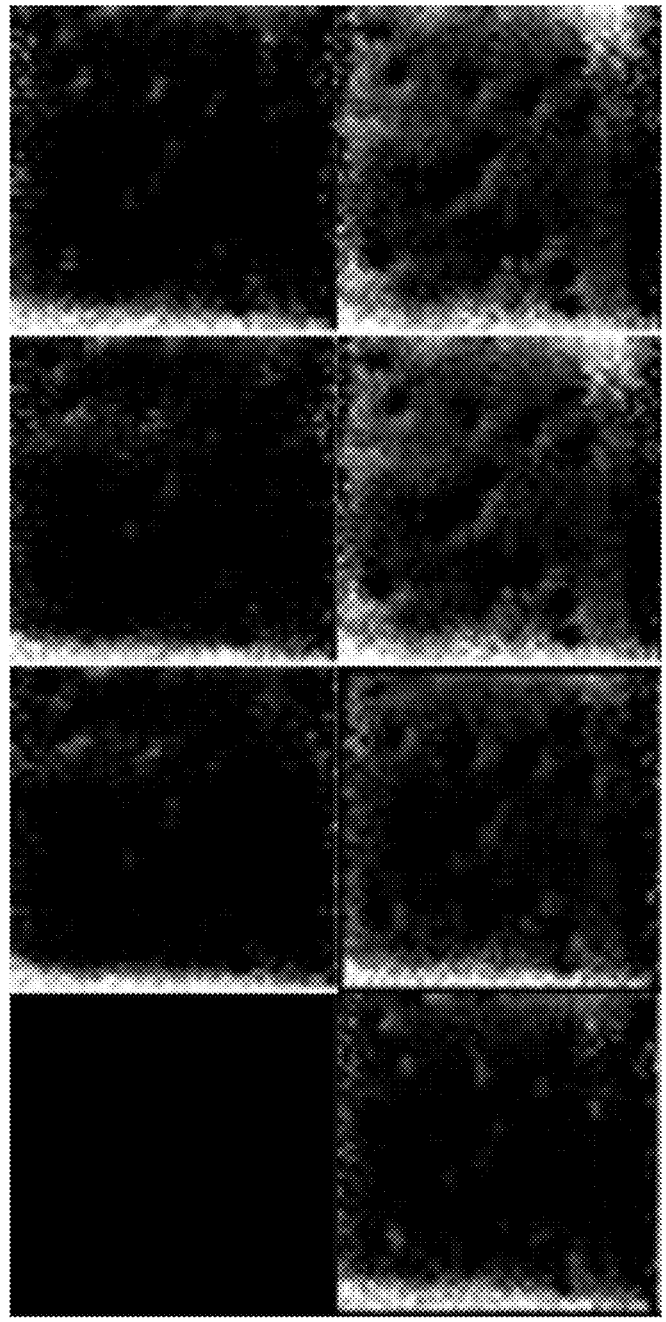

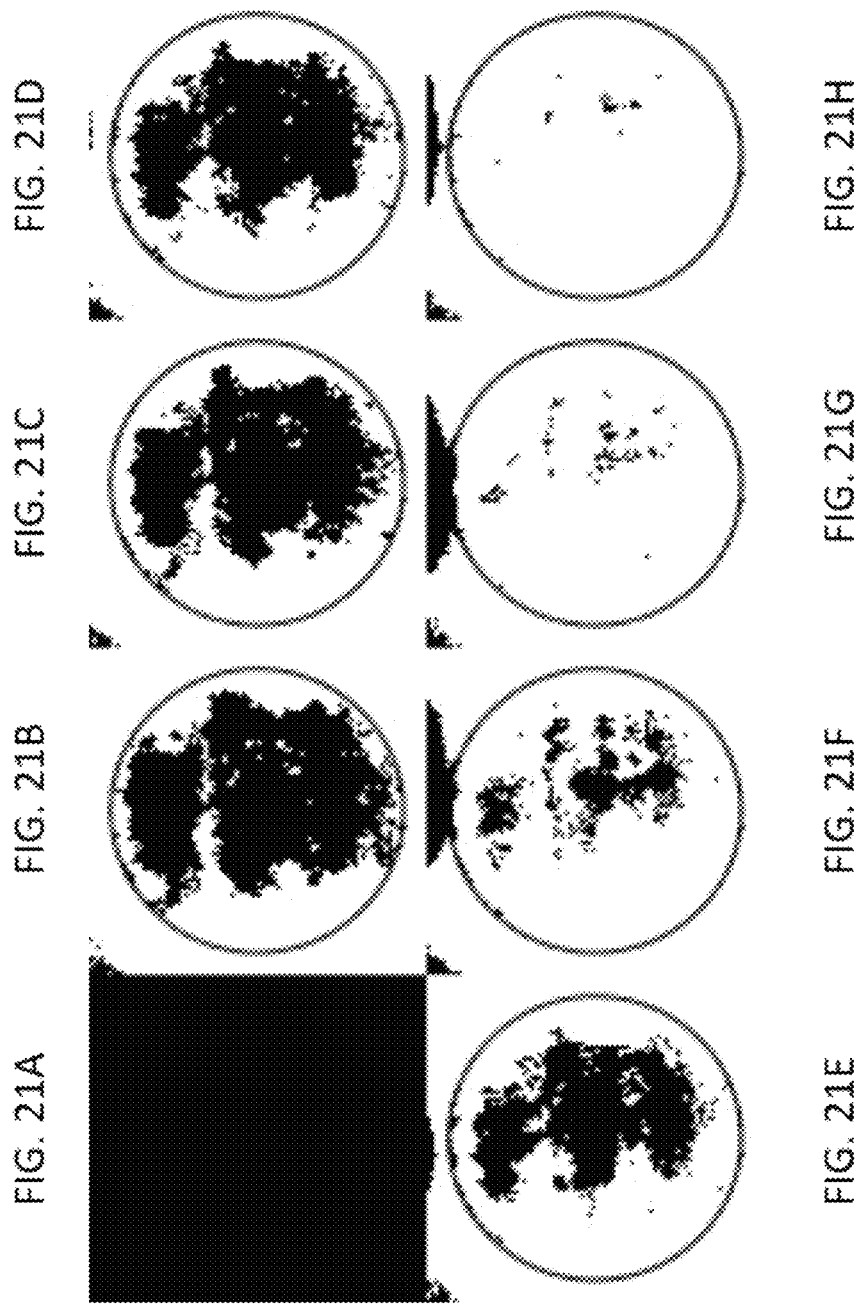

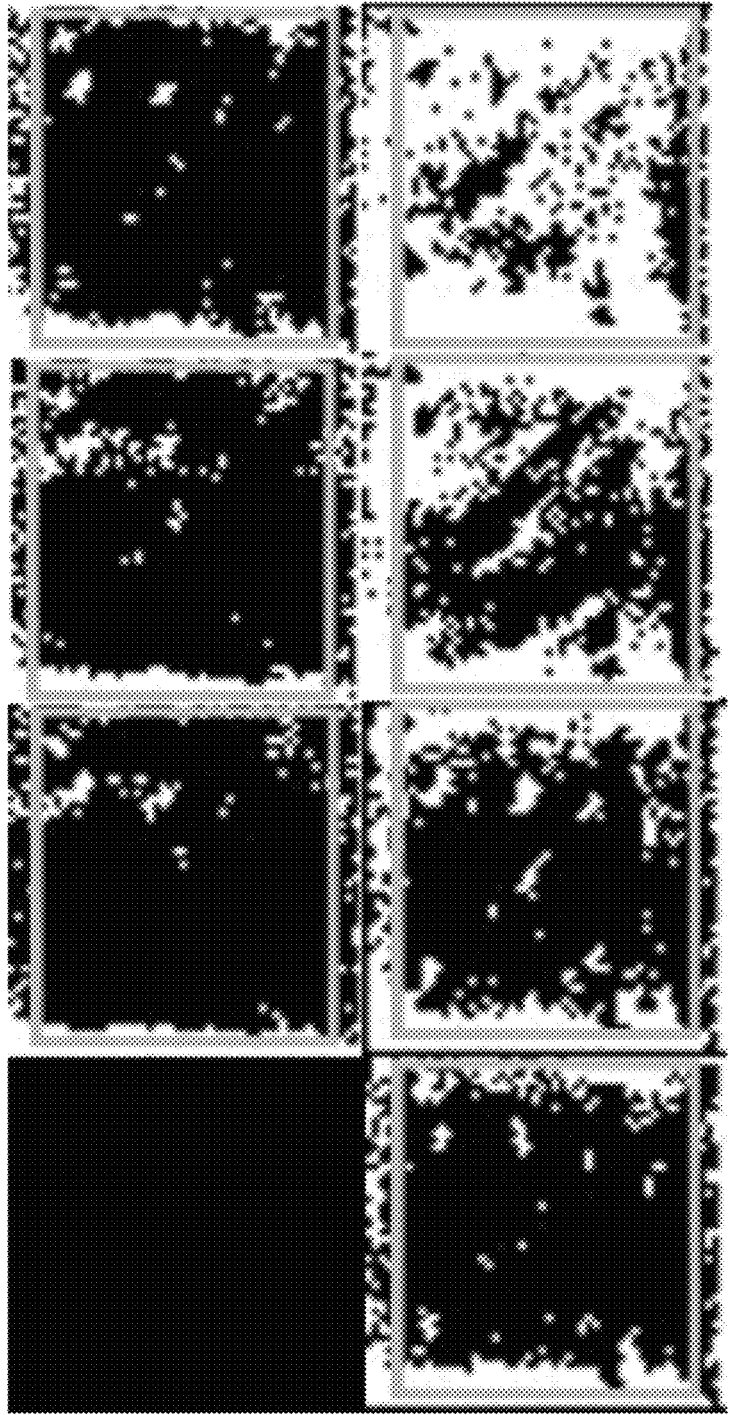

METHODS AND APPARATUS FOR THE NON-DESTRUCTIVE MEASUREMENT OF DIFFUSION IN NON-UNIFORM SUBSTRATES

CROSS-REFERENCE TO RELATED APPLICATIONS

This application claims the benefit of U.S. Provisional Patent Application No. 61/408,408 filed Oct. 29, 2010 and is a continuation in part of U.S. patent application Ser. No. 13/024,406 filed Feb. 10, 2011, which is a continuation of U.S. patent application Ser. No. 11/965,045 filed Dec. 27, 2007, now U.S. Pat. No. 7,906,975, and claims the benefit of U.S. Provisional Patent Application No. 60/898,208, filed Jan. 30, 2007, the entireties of which are incorporated herein by reference.

FIELD OF THE INVENTION

This invention relates to methods and apparatus for performing terahertz (herein referred to as "THz") spectroscopy. More specifically, the invention relates to the imaging of diffusion of liquid through non-uniform materials such as cork.

BACKGROUND OF THE INVENTION

The quality of cork enclosures is determined by the presence and size of defects, voids, or cracks. These defects can harbor impurities, which in turn can cause cork taint. Cork taint typically spoils 3%-5% of all wines that use natural cork as a stopper.

Most corks are punched with the long axis of the cork perpendicular to the lenticels. The lenticels allow for the interchange of gases between the atmosphere and the interior structure of the cork tree. It has been shown that impurities do not quickly permeate down the length of the cork, but propagate much more quickly perpendicular to the long axis. Only when contaminated parts of the cork are in direct contact (approximately the first few millimeters of cork) with the contained liquid, such as wine, does transfer of contaminants, and cork taint, take place. The extraction and migration of non-volatile chemicals from cork depend on the local diffusion rates. Therefore, an understanding of the diffusion of liquid in cork is important. The presence of cracks, voids, and defects may increase diffusion. The presence of these potentially highly anisotropic features in the cork affects the measurement of absorbable contaminants such as trichloroanisole (TCA) in wine corks.

TCA is one of the primary contributors to off-flavors or cork taint in wine. The presence of TCA in natural cork is presently determined by a cork soak method in which cork samples are immersed in a neutral white wine which extracts or "releases" the TCA which has enough mobility in the cork structure to contaminate the wine. After a soak of typically 24 hours, the wine is then tested for the presence of TCA using gas chromatography. Herve, E., et al., ASEV Annual Meeting Reno, Nev.: http://www.corkqc.com/asev/asev2-2.htm.1999.

There are methods for determining the diffusion coefficient of water in natural corks. In one method, small cork samples are submerged in water. As a function of time, the dimensions and mass of the sample are measured to determine the change in volume and mass of the sample due to the diffusion of water into the cork. A second method involves inserting two metallic electrodes into the cork and measuring the electrical resistance between them. One side of the sample is placed in contact with a water reservoir. Over time, water diffuses from the reservoir into the cork's structure. When water is absent from the proximity of the electrodes, the resistance is very high. As the concentration of water increases between the two electrodes, the resistance dramatically decreases. These techniques have at least two inherent limitations: (a) they are inherently invasive detection methods and (b) they measure essentially average diffusion properties. In the cork submersion method, samples must be continually removed from the soak in order to record data. Using the electrical method, the cork structure must be punctured. Both methods measure average sample properties. For example, the cork submersion method measures the total volume and weight change of the sample. Some degree of localized measurement is possible with the electrical method by using multiple sets of electrodes. However, a spatially continuous measurement is not possible. The electrode method is particularly troublesome since the shape of the resistance versus time curves depends upon the depth of the electrode placement in the cork—an artifact of the inhomogeneity of the cork. Consequently, the electrode technique does not show an appreciable anisotropy in the radial and non-radial diffusion coefficient.

There is no visual indication that a particular cork prior to bottling will result in cork taint or that a previously bottled wine is tainted. Methods and apparatus for non-destructively evaluating diffusion characteristics of solid materials such as cork would be useful. Wine producers, bottlers, dealers, collectors and connoisseurs would greatly benefit from a non-destructive method and apparatus to determine the likelihood of a cork causing taint prior to the cork being used to seal a bottle and/or the likelihood a given cork in a sealed bottle would be a cause of taint.

SUMMARY OF THE INVENTION

The present inventors have surprisingly found that terahertz (THz) spectroscopy can be used to detect the presence of a variety of constituents including structural entities and variations thereof including but not limited to voids, structures, anomalies, defects, density variations or locations in the sample or cork in which chemical entities such as TCA and MMDA, or biological entities such as bacteria or mold could exist or propagate, which could ultimately result in tainted wine. In the case of natural cork, the large volume of the cork cell lumen and relatively low humidity enables the material to be compressible, yet exhibit fairly high THz transmission. As the cork absorbs liquids such as water, the intrinsically high THz absorbance of liquids enables THz imaging to follow the progression of the liquid as it permeates and diffuses through the cork structure.

Since the majority of wines are bottled using natural cork, devices and/or systems that can non-destructively detect a variety of constituents as described above and obtain images relating to diffusion characteristics of liquid would be of tremendous value to wine producers, distributors, collectors, restaurants, etc. THz spectroscopic devices, apparatus and methods are provided herein adapted to detect constituents and to image diffusion characteristics of solid structures such as cork.

In accordance with one aspect of the present invention an apparatus is provided which employs THz spectroscopy and/or imaging to measure the average diffusion coefficients for a material such as cork. In accordance with another aspect the apparatus may be used to image the localized presence of water in the structure to produce time-dependent images of water propagation in the structure.

In accordance with a further aspect methods are disclosed which employ THz spectroscopy and/or imaging to measure the average diffusion coefficients for a material such as cork. In accordance with another aspect the methods may be used to image the localized presence of water in the structure to produce time-dependent images of water propagation in the structure. Unlike previous methods, in which cork samples are carefully selected to eliminate obvious cracks, defects, or voids in the sample, the presently disclosed methods and devices do not require a-priori selection of cork sample in order to measure the average diffusion coefficients. Moreover, the THz imaging enables one to visualize and characterize the effect of lenticels, cracks, voids, and defects on the local diffusion of water.

In one embodiment the methods provided herein enable the prediction or estimation of the likelihood that contaminants are present or may become present in a material. A cork with a high diffusion rate may be indicative of an increased likelihood the contents of a container closed with the particular cork is or will be tainted. Similarly, the methods herein enable the skilled artisan to test a material such as a cork for structural variations such as voids, structures, anomalies, defects, density variations or locations in the cork in which TCA or some other manifestation (e.g. MDMP, mold, bacteria) is growing or could grow before it is used as a stopper for the wine bottle. Methods may include identifying, categorizing and/or analyzing data, such as a change in radiation, or one or more distinct THz absorption values, peaks or spectra associated with the various structural variations in the material or cork in which contaminants that promote spoilage could exist or propagate. The terms data, change in radiation, THz absorption values, peaks or spectra are used interchangeably in the current disclosure.

In one embodiment a method of nondestructively measuring the diffusion of water in a material using THz time-domain imaging of at least a portion of the interior of the material includes introducing THz radiation to a material; receiving the THz radiation transmitted through the material; collecting spectral data of the received THz radiation by acquiring the image one pixel at a time and recording the spectrum of THz radiation at each pixel; generating a THz image of at least a portion of the interior of the material; recording the image of the material; subsequently, injecting liquid into the material; and recording a THz image of the liquid-injected material at selected intervals. The material prior to liquid injection may be substantially dry.

"Substantially dry" means and includes a material that has the appearance and tactile feel of dryness and has not been subjected to soaking, immersion or wetted for a period of time adequate to permit diffusion. Thus, a "substantially dry" material could include some internal moisture or wetness not apparent to the naked eye or touch. An example of a material material is cork.

In accordance with one embodiment the method may include a step of translating the material out of a path of the THz radiation and recording a background time-domain scan to obtain a reference prior to the acquisition of each THz image. The method may include calculating the THz frequency dependent absorbance for each pixel in the image as $$A(\omega) = -\ln(T(\omega)) = -\ln(|E_s(\omega)|/|E_r(\omega)|)$$

where $|E_r(\omega)|$ and $|E_s(\omega)|$ are the magnitudes of THz electric fields as calculated by the Fourier transform of the time-domain data of the reference and material, and $T(\omega)$ is the transmission through the material.

The method may further include averaging the absorbance over a specified bandwidth range to obtain a single value at each pixel position and construct an image. A preferred specified bandwidth for image processing is 0.65-0.70 THz.

In one embodiment the method may include stitching together the recorded images to create a time-lapse movie that shows the diffusion of liquid through the material. Images of the material that are images of liquid-injected material may be subtracted to provide a diffusion-only picture. A Gaussian filter and stabilization algorithm may be applied to the images to smooth spatial noise.

In yet another embodiment the method may include extracting a location of a wavefront by processing images to monitor which pixels exhibit an absorbance value above a fixed threshold.

BRIEF DESCRIPTION OF THE DRAWINGS

To assist those of ordinary skill in the relevant art in making and using the subject matter hereof, reference is made to the appended drawings, wherein:

FIG. 4a: 0.1-0.3 THz; FIG. 4b: 0.3-0.5 THz; FIG. 4c: 0.5-0.8 THz; and FIG. 4d 0.8-1.0 THz. Each pixel in the images is 500 μm square. The overall size of the THz cork image is ~19 mm;

FIG. 6 (a) depicts the measured THz time-domain waveform (gray) through a 4.4 mm thick cork sample. The reference waveform (black) is taken with the sample removed. FIG. 6(b) depicts corresponding amplitude as a function of frequency after Fourier transforming the time-domain data. Sharp structures near 0.57, 0.7, 1.1 THz and other frequencies in the reference waveform are artifacts of absorption by water vapor in the atmosphere;

FIGS. 11A-11C depict visible images of cork cross sections for front (FIG. 11A) and back (FIG. 11B) surfaces, the back surface image being flipped horizontally so that the composite image FIG. 11C) can be used to visualize the composite structure of the two surfaces in transmission;

FIG. 12 depicts THz absorbance (0.65-0.70 THz) through the dry cork composite visible image of front and back surfaces of cork sample according to FIG. 11C. Regions labeled 0 through 9 are analyzed for the local change in absorbance with time as the water diffuses thorough the cork;

FIGS. 17A-17H graphically depict THz absorbance (0.65-0.7 THz) through cork cross-section at 0 hr (dry cork, FIG. 17A), 10.9 hr (FIG. 17B), 21.9 hr (FIG. 17C), 33 hr (FIG. 17D), 44 hr (FIG. 17E), 55.6 hr (FIG. 17F), 78.2 hr (FIG. 17G), and 93.6 hr (FIG. 17H), (left to right, top to bottom progression) respectively; dark regions correspond to low absorbance while bright regions correspond to high absorbance; bright regions outside of the cork are highly transparent in the dry image since the water was not added to the sample chamber; dark regions near the top of the sample chamber result from the level of water dropping in the chamber due to evaporation;

FIGS. 19A-19H graphically depict water-only diffusion (dry cork image subtracted) through the cork material of FIGS. 17A-17H;

FIGS. 20A-20H graphically depict water-only diffusion (dry cork image subtracted) through the cork sample of FIGS. 18A-18H;

FIGS. 21A-21H graphically depict tracking of the diffusion front through the cork sample of FIGS. 17A-17H using a 0.5 absorbance threshold, in an embodiment in which an absorbance of 0.5 through the 4 mm sample corresponds to a 12% weight increase of water; the dark circle indicates the location of the sample; and FIGS. 22A-22H graphically depict tracking of the diffusion front through the cork sample of FIGS. 18A-18H in the axial growth direction using a 0.3 absorbance threshold, in an embodiment in which an absorbance of 0.3 through a 5 mm sample corresponds to a 5.7% weight increase in water; the rectangle indicates the location of the sample.

Figure 1:
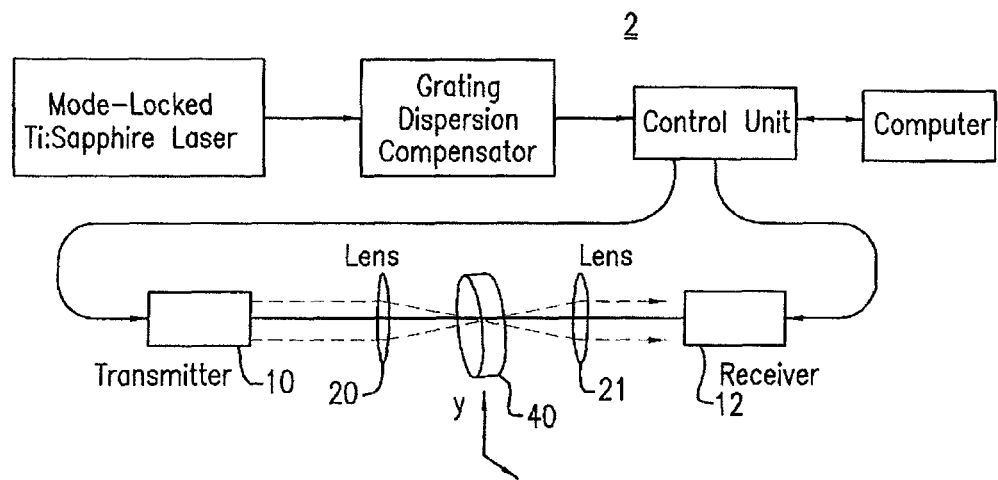
FIG. 1 depicts a schematic of a THz transmission system to measure THz spectra through a material such as cork in accordance with at least one embodiment of the present invention.

It should be noted that the appended drawings illustrate only typical embodiments of this invention and are therefore not to be construed as limiting of its scope, for the invention may admit to other equally effective embodiments. Where possible, identical reference numerals have been inserted in the figures to denote identical elements.

DETAILED DESCRIPTION OF THE INVENTION

In the following description, for purposes of explanation, specific numbers, materials and configurations are set forth in order to provide a thorough understanding of the invention. It will be apparent, however, to one having ordinary skill in the art that the invention may be practiced without these specific details. In some instances, well-known features may be omitted or simplified so as not to obscure the present invention. Furthermore, reference in the specification to phrases such as "one embodiment" or "an embodiment" means that a particular feature, structure or characteristic described in connection with the embodiment is included in at least one embodiment of the invention. The appearances of phrases such as "in one embodiment" in various places in the specification are not necessarily all referring to the same embodiment.

THz radiation is readily transmitted through most non-aqueous, non-metallic materials. Constituents such as structural entities and variations thereof such as voids or density variations as well as the chemical and biological entities that can exist or propagate in those structural entities can be detected by THz radiation. By identifying and categorizing signatures of structural variations within the cork in which the chemical or biological entities can exist or propagate which are responsible for cork taint, resulting in what is known as "corked" wine, THz spectroscopy can be used to determine the potential for individual corks to spoil a wine prior to bottling, or spoilage prior to uncorking or opening a wine bottle. In addition, THz spectroscopy can be used to measure not only the average diffusion coefficients for a cork sample, but also image the localized presence of water in the cork structure to produce time-dependent images of water propagation in the cork structure.

Now referring to FIG. 1, in one embodiment an apparatus 2 is shown that is adapted to detect, identify, and/or quantify structural entity constituents or a constituent in a sample 40 by THz spectroscopy, preferably prior to the sample 40 being inserted into a container. Apparatus 2 includes a radiation source 3, grating dispersion compensator 5, control unit 7, transmitter 10, receiver 12 and lenses 20 and 21. A computer is optionally operably connected to apparatus 2, preferably to control unit 7. Radiation from the THz transmitter (THz TX) 10 propagates through the sample 40 and lenses 20 and 21 and is captured by the THz receiver (THz Rx) 12.

The radiation source 3 may be any suitable means of generating a signal or terahertz frequency such as but not limited to a laser, which may be used to generate and/or detect pulses of THz radiation. For example, a mode-locked Ti:sapphire laser may be employed. Alternate embodiments may include micro-fabricated antenna structures to detect pulses of THz radiation. As will be apparent to those having skill in the art, the transmitter 10 may include the radiation source 3, grating dispersion compensator 5, control unit 7 in a single unit. The receiver 12 is any suitable means of receiving and processing the terahertz radiation that is transmitted and passes through the sample 40.

The sample 40 to be analyzed may be, by way of example only and without limitation, a natural or synthetic cork or a wine bottle. Sample 40 is typically predominantly non-metallic and non-aqueous media.

As used herein, a constituent may be any substance that has a unique THz signature. The constituent may be any contaminant or combination of constituents or substances that are naturally occurring, or added substances that are included by design or chance. By way of example only, constituents may include structural entities, chemical entities and/or biological entities. The term constituent includes structural variations such as voids, structures, anomalies, defects, density variations or locations in the sample 40 (for example without limitation, cork) in which constituent(s) including chemical or biological entities exist or could propagate. In addition, constituents can be, by way of example only and without limitation, chemical or biological entities including but not limited to bacteria, mold, TCA, or some other manifestation (e.g. MDMP) that can be detected and monitored.

THz radiation used may vary in pulse duration and composition of spectral components. A THz pulse may have a duration in a range from about 1 femtosecond to about 100 nanoseconds. For example, a THz radiation pulse may be 1 to 100 picoseconds. The spectral components of the laser may fall within a range from about 0.01 THz to about 5.0 THz. For example, some embodiments include lasers emitting THz radiation having a spectrum in a range from about 0.1 THz to about 2.5 THz.

Lenses 20 and 21 are employed in some embodiments to focus the THz radiation. For example, the THz radiation may be focused to a 1 mm spot using one or more lenses. Samples 40 to be analyzed may be positioned to allow the focused radiation to contact the sample 40. In some embodiments, the sample 40 may be mechanically scanned using computer controlled translation stages. Radiation passing through the sample 40 may be focused onto a THz detector. In some embodiments, an image may be acquired one pixel at a time and/or may include recording a spectrum of the THz radiation at each pixel.

Figure 2:
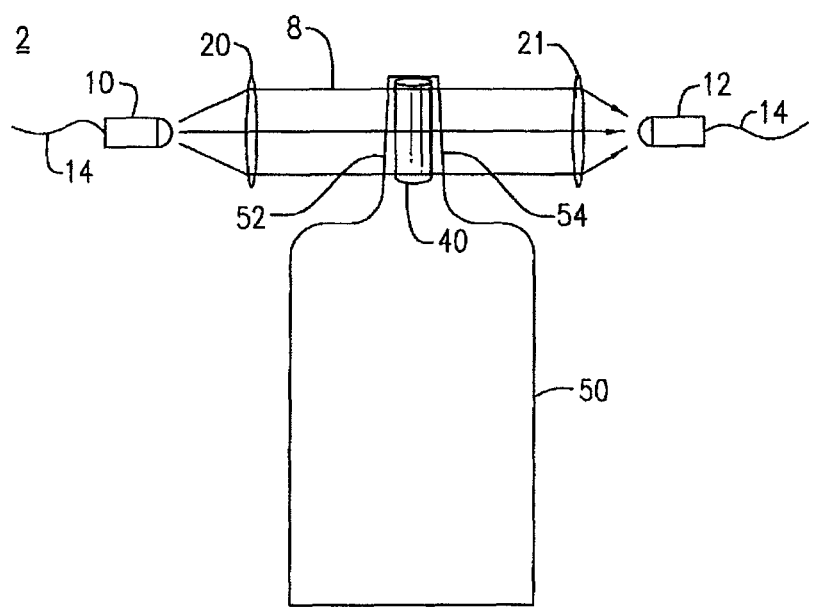
FIG. 2 depicts a schematic of a THz spectroscopy device adapted to scan a material in accordance with at least one embodiment of the present invention.

Now referring to FIG. 2, in accordance with another embodiment, a system 2 employing THz radiation is provided for detecting, identifying, and/or quantifying one or more constituents in a sample 40. The sample 40 may be independent or acting as a sealing apparatus in a container 50. A THz transmission system 2 is adapted to measure the THz spectrum of a constituent or constituents present in a sample 50. In this embodiment, a signal or electromagnetic radiation 8 in the THz frequency range from the THz source and/or THz transmitter 10 is propagated through the sample 40. The radiation 8 that passes or propagates through the sample 40 is then captured by the THz receiver 12. The receiver 12 is preferably adapted to transmit the data and/or THz absorption peaks to an analytic device for analysis and/or computation. The data can then be compared to known THz absorption peak spectra of various constituents to determine which, if any, constituents are present in the sample 40.

In one embodiment, a fiber optic pigtail 14 may be connected to the THz TX 10 and the THz RX 12. A fiber optic pigtail 14 is a short optical fiber that is permanently attached to a fiber optic device. This fiber optic device can include a source, a detector, a transmitter such as a THz TX 10, or another fiber optic device as is known to those skilled in the art. The pigtail 14 may be connected to the optical connector or a THz RX 14 at the other end.

System 2 may detect the constituents present in a sample 40 that has been inserted into a container 50. For example, a sample 40 may be a cork or other sealing apparatus for a sealed container such as but not limited to a wine bottle. In this embodiment, radiation 8 from a THz TX 10 propagates through both the container 50 and the sample 40. The radiation 8 propagates through a first lens 20, a first wall 52 of the container 50, the sample 40 and then through a second wall 54 of the container 50. The radiation 8 then passes through a second lens 21 before it is captured by a THz RX 12.

Alternatively, the radiation 8 may be propagated at an angle so that the radiation 8 is sent through the first wall 52 of the container 50, through the sample 40 and out the top of the sample 40 such that the radiation 8 never passes through the second wall 54 of the container 50.

Figure 3:
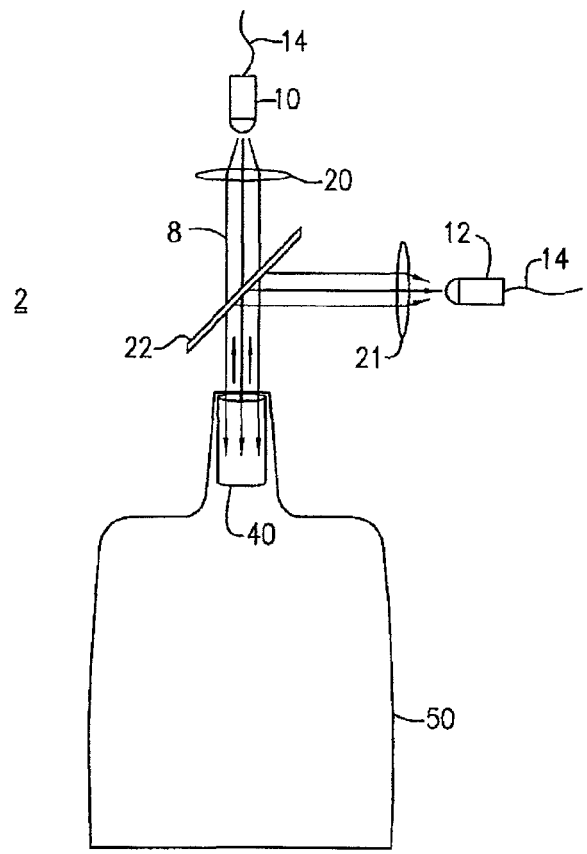
FIG. 3 depicts a schematic of a THz spectroscopy device adapted to scan a material in accordance with at least one embodiment of the present invention.

Now referring to FIG. 3, in another embodiment of the present invention a system 2 is provided that detects constituents present in a sample 40 such as a sealing apparatus that has been inserted into a container 50. This embodiment differs from the embodiment of FIG. 2 in that radiation 8 from a THz TX 10 propagates solely through the sample 40 without passing through any part of the container 50. The radiation 8 from the THz TX 10 propagates through a first lens 20, then through an optical device such as a beamsplitter 22. The beamsplitter 22, which may be a partially reflecting mirror, allows the radiation 8 to pass through completely and propagate into the sample 40. Some of the radiation 8 then reflects back up through the sample 40 and back to the beamsplitter 22 which then acts as a directional coupler to direct the radiation 8 to a second lens 21 and then to a THz RX 12. Again, in additional embodiments, a fiber optic pigtail 14 may be operably connected to the THz TX 10 and the THz RX 12.

In another embodiment the present invention methods are provided to detect, identify and/or quantify constituents in a sample using THz technology. Methods are provided for detecting and/or identifying structural variations such as voids, structures, anomalies, defects, density variations or locations in the sample, such as a cork, in which bacteria, chemicals or mold could exist or propagate, and the identification and/or a determination of the likelihood that a constituent, subconstituent and/or contaminant is present.

In accordance with such methods, a signal or electromagnetic radiation in the THz frequency range from a THz source or THz transmitter is introduced. The signal or radiation that passes or propagates through the sample is then captured by a THz receiver. The receiver transmits the data, signal and/or THz absorption peaks to an analytic device for analysis and computation. The THz absorption peaks may then be compared to known THz absorption peak spectra for a determination of the constituents inside the sample.

The sample to be tested may be independent or acting as a sealing apparatus in a container. The apparatus used to practice the methods, including the THz source or the THz transmitter, the sample and the THz receiver, can be assembled in various configurations. The methods may employ apparatus such as those described hereinabove. For example, the methods may employ apparatus wherein the THz source and/or THz transmitter, the sample and the THz receiver are set up so that the radiation passes through one or more walls of the container and through the sample before being captured by the THz RX. One such configuration is a parallel configuration as depicted in FIG. 2.

In yet other embodiments, the methods may employ apparatus wherein radiation from the THz source and or THz transmitter pass through the sample and to the THz receiver without contacting the container as depicted in FIG. 3.

EXAMPLES AND EXPERIMENTS

In one example, the THz transmission of cork sample was measured employing apparatus as depicted in FIG. 1. A mode-locked Ti:sapphire laser was used to generate and detect pulses of THz radiation in micro-fabricated antenna structures. The pulse of Terahertz radiation was roughly a few picoseconds in duration and contains spectral components from about 0.1-2.5 THz. The THz radiation was focused to a ~1 mm spot size using lenses. The sample was placed at the focus of the radiation and mechanically scanned using computer controlled translation stages. After passing through the sample, the radiation was focused onto a THz detector. The image was acquired one pixel at a time; at each pixel, the spectrum of THz radiation was recorded.

Figure 4:
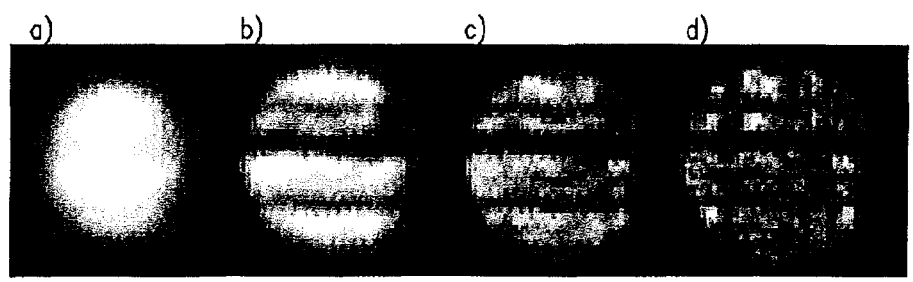
FIG. 4 depicts THz transmission images of the cork material depicted in FIG. 5A for THz bandwidths as follows.
Figure 5A:
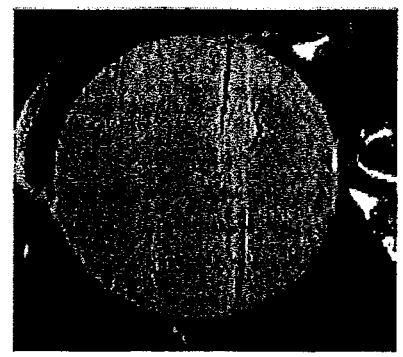
FIG. 5A is a photograph of a cork material.

Now referring to FIG. 4, THz images were generated by measuring the THz power transmitted in a specific THz bandwidth. FIG. 4 depicts THz transmission images of the cork sample depicted in FIG. 5A for THz bandwidths as follows: FIG. 4a: 0.1-0.3 THz; FIG. 4b: 0.3-0.5 THz; FIG. 4c: 0.5-0.8 THz; and FIG. 4d 0.8-1.0 THz. Each pixel in the images is 500 µm square. The overall size of the THz cork image is ~19 mm. Bright pixels correspond to high transmission, while dark pixels correspond to low transmission. The THz image of the cork shows the internal structure of the cork, a 4.48 mm thick cork sample from a 1997 Riston Estates Cabernet Sauvignon as depicted in FIG. 5a.

Figure 5B:
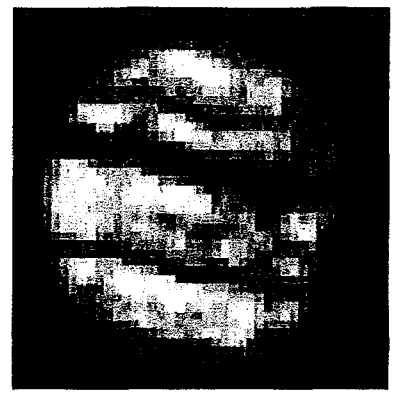
FIG. 5B is a THz transmission image of the cork material of FIG. 5a using the same THz bandwidth as used in FIG. 4c.

Contrast in the image and the prominence of the internal structure depends on the band of THz frequencies used. The contrast in the THz image may be due to several effects in some embodiments; the two most common are absorption and scattering. Now referring to FIG. 5b, which is a THz transmission image of the cork sample of FIG. 5a using the same THz bandwidth as used in FIG. 4c), except that the cork sample was dried overnight in a desiccant, it is observed that residual water trapped in the cork structure may affect absorption. The image after drying (FIG. 5b) illustrates that the apparent structure is still present.

Scattering of electromagnetic radiation can be thought of as occurring on two different spatial scales. When the size of the scattering object is much smaller than the wavelength of radiation (Rayleigh scattering), the scattering which is strongly wavelength dependent, scales as $v^4$ where $v$ is the electromagnetic frequency. When the wavelength is comparable to the size of the scattering object (Mie scattering), the efficiency of scattering is greatly enhanced and sensitive to the size of the scattering object.

Since the typical size of a cork cell (~40-60 µm) is much smaller than the wavelength the THz radiation used (1 THz corresponds to 300 µm, 0.1 THz corresponds to 3 mm), the observed contrast in the THz images as the THz frequency is increased, and the wavelength is decreased, is due to scattering of THz radiation by anomalies in the regular pattern of the cork cell structure. In some embodiments, anomalies may be lenticels or some structural defect in the cork cell pattern; or may be locations at which microorganisms and TCA could be concentrated due to the relative ease of transport of liquids and gases along the lenticels.

In accordance with another set of experiments, natural cork samples were acquired from a variety of bottled wine varietals. Samples were dried in ambient air for several days. Samples roughly 4 mm thick were cut from the end of the cork that was not in contact with the wine. As a control, samples of cork that had not been used in the bottling process were also tested.

Figure 6:
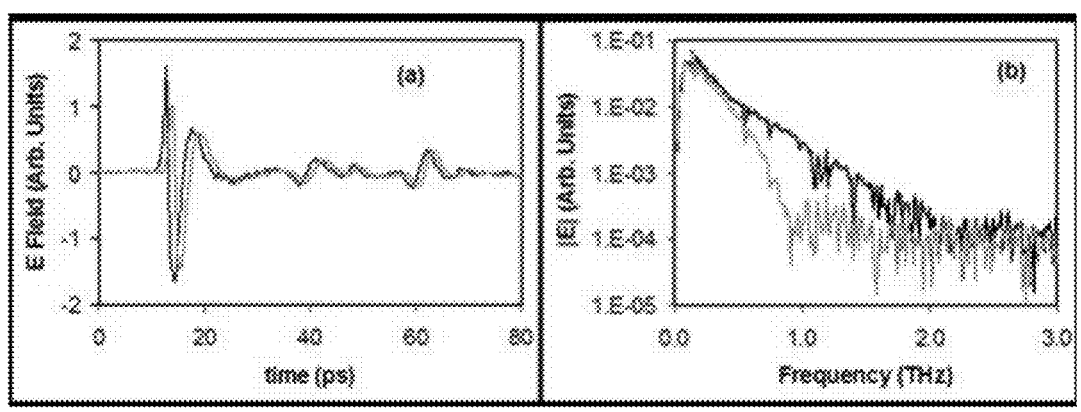
FIG. 6 depicts graphical representations of THz time-domain waveforms in accordance with at least one embodiment of the present invention.

A T-Ray 2000 Spectroscopy system (Picometrix, Inc) was used in the transmission mode to measure the THz time-domain waveform. Details of the THz time-domain method may be found in D. Mittleman, "Terahertz Imaging" in *Sensing with Terahertz Radiation*, D. Mittleman Ed. (Springer, 2003). A pair of silicon lenses (3 inch focal length) were employed to focus the THz radiation to a spot at which the sample was placed. The imaging system consisted of a pair of computer controlled linear translation stages (1 µm resolution). The THz images were acquired by recording the THz transmitted pulse at each sample position. Typical THz time-domain waveforms are shown in FIG. 6. Spectral information as a function of frequency, both phase and amplitude, was acquired through a Fourier transform of the time-domain data.

As shown in FIG. 6, the slight time shift in the arrival of the peak of the pulse is indicative of the real index of refraction of the cork sample. Typical values are between 1.07 and 1.1. In examining the magnitude of the THz electric field as a function of frequency, it is clear from the reference data that the THz amplitude approaches the noise limit of the THz system at approximately 2 THz. After passing through the cork sample, data beyond about 0.95 THz was in the noise for this particular sample location. For the spectroscopic data presented herein, only data within the signal-to-noise of the system is plotted for purposes of clarity.

THz images were formed by measuring the full time-domain waveform within an 80 ps time window. The sample was mechanically scanned in two directions at the focal point of the THz to generate an image one pixel at a time. Typical step sizes were 100-500 µm.

Results and Discussion

Figure 7:
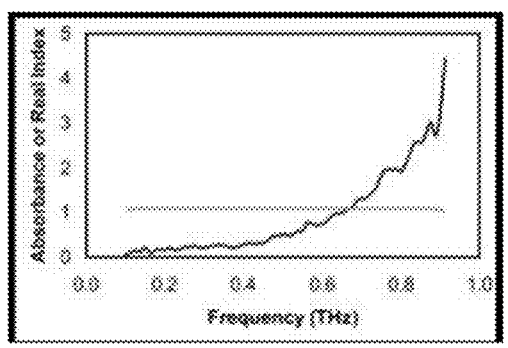
FIG. 7 is a graphical representation of the calculated frequency dependent absorbance (black) and the real index of refraction (gray) for the time-domain waveforms of FIG. 6.

There are many methods for analyzing the THz waveforms and generating a THz image. For example, one can measure the total transmitted THz power, the transmitted power within a given frequency interval, the change in the arrival time of the THz pulse, etc. At each pixel in the THz image, the THz phase and amplitude is normalized to the phase and amplitude of the reference waveform. FIG. 7 shows the corresponding absorbance $$A(v) = -\ln(T(v)) = -\ln(|E_s(v)|/|E_r(v)|) = \mu L$$

at one pixel where $T(v)$ is the frequency dependent transmission referenced to a THz spectra with the sample removed. $|E_s|$ and $|E_r|$ are the magnitudes of the THz electric fields for the sample and reference, respectfully. L is the thickness of the sample and $\mu$ is defined as the attenuation coefficient.

FIG. 7 also shows the frequency dependence of the real index of refraction as calculated by $$n_{real}(v) = \frac{(\phi_r(v) - \phi_s(v))c}{2\pi v L} + 1$$

where $\phi_s$ and $\phi_r$ are the Fourier transformed frequency dependant phases of the sample and reference waveforms, respectfully, c is the speed of light, L is the thickness of the sample, and $v$ is the frequency. The real index of refraction is essentially constant over the measured range.

Diffusion Methods and Apparatus

The diffusion of water in natural corks is anisotropic in the radial, axial and tangential directions. Pereira, Helena, *Cork: Biology, Production and Uses*. New York: Elsevier, 2007. ISBN-13: 978-0-444-52967-1. The radial direction corresponds to the direction of the radial growth of the Cork Oak tree. The axial direction is parallel to the tree's axis. The transverse direction corresponds to the direction along the circumference of the tree's diameter. The anisotropy in diffusion can be attributed to several effects. For example, it is well-known that the diffusion coefficient in the radial growth direction is larger than that of the other two directions due to the presence of lenticular channels (pores) that run parallel to the radial growth direction. Pereira, H., *Cork: Biology, Production and Uses*. New York: Elsevier, 2007. ISBN-13: 978-0-444-52967-1; Rosa, M. E. and Fortes, M. A., *Water Absroption by Cork*, 4, 1993, Wood and Fiber Science, Vol. 25, pp. 339-348. The lenticular channels enable water and gases to diffuse through the cork. In addition, one would expect the presence of cracks, voids, and defects to increase the diffusion. The presence of these potentially highly anisotropic features in the cork implies a highly variable local diffusion rate. The lenticular structure, cracks, voids and other defects affect the measurement of absorbable TCA in wine cork stoppers. The regions of the cork from which TCA can be released should be dependent on the local diffusion rates of wine/water. Similarly, the extraction and migration of non-volatile chemicals from the cork will depend on the local diffusion rates. Gonzalez-Adrados, J. R, et al., *Cork-Wine Interaction Studies: Liquid Absorption and Non-Volatile Compound Migration*. 3, 2008, J. Int. Sci. Vigne Vin, Vol. 42, pp. 161-166.

THz time-domain spectroscopy has been used to measure the diffusion of solvents in polymeric materials. Jordens, C., et al., *Investigation of the water absoption in polylamid and wood plastic composite by terahertz time-domain spectroscopy*. 2010, Polymer Testing, Vol. 29, pp. 209-215, describes measurements of water absorption and diffusion in polyamide and wood plastic composite using THz time-domain spectroscopy. With polymers as well as natural cork, one can use THz spectroscopy to differentiate between bound water (water molecules bound to the sample material) or free liquid water. The dielectric properties of bound and free water differ due to the fact that the molecules' vibrations are slightly altered by their local environment. In particular, bound water has a lower refractive index and absorption coefficient compared to free water. As described in Jordens, above the fiber saturation point of the plastics, free water accumulates in the voids and cavities in the composite material. Since their measurements are taken for water levels below the saturation point, their THz measurements suggest that only bound water is present in the studied materials. They model diffusion using the weight percent increase in their sample $$Wt\%(t) = Kt^m \qquad (1)$$

where K and m are constants and t is time. When m=½, the diffusion follows Fick's diffusion equations. A fit of the measured total water absorption versus time in polyamide follows the Fick diffusion model with a diffusion coefficient of $3.4 \times 10^{-13}$ m$^2$/s.

THz spectroscopy has also been used to measure the diffusion of acetone in polycarbonate and polyvinylchloride polymers. Obradovic, J., et al., *The use of THz time-domain reflection measurements to investigate solvent difusion in polymers*. 2007, Polymer, Vol. 48, pp. 3494-3503. In these measurements, a THz reflection geometry is used to track the progression of the dry polymer/liquid interface over time. Pulses of THz radiation reflect from dry polymer/liquid interface. As the boundary of the diffusing liquid moves through the material, the reflecting pulses are detected earlier in time indicating motion of the liquid. In analyzing the kinetics of the wavefront, an equation similar equation to Eq. (1) is employed. Obradovic, J., et al. Since the liquid absorption is typically correlated with the front position of the penetrating liquid, one may replace the left hand side of the equation with the time dependent depth of penetration of the liquid to analyze the diffusion.

For use in various embodiments of the presently disclosed subject matter, in order to extract a diffusion coefficient for the cork, a relationship may be established between the measured THz absorbance and the concentration of water in the cork. To extract this relationship, one needs to know the frequency dependant dielectric permittivity of the cork, as well as water, and use a model to predict the effective dielectric properties of wet cork in the THz range as a function of water content. It is known that the cell walls of cork reach saturation when the weight of the initially dry cork increases by 60% relative to the dry cork weight. Rosa and Fortes, ibid. Based on their data, Rosa and Fortes conclude that water predominately diffuses through the cork via the cork cell walls before it fills the internal volume of the cork cell. For multiple embodiments of the presently disclosed subject matter, a 60% weight increase is employed as the threshold for determining the diffusion coefficient of the cork. As will be shown below, the THz absorbance values suggest that we are well below the saturation point on average throughout the cork.

In order to model the effective dielectric properties of mixtures in the THz range, several methods have been proposed. See, Scheller, M., et al., *Modelling heterogeneous dielectric mixtures in the terahertz regime: a quasi-static effective medium theory*. 2009, J. Phys. D: Appl. Phys., Vol. 42, pp. 065415-10. As an example, Balakrishnan, et al., *Sensing the hygroscopicity of polymer and copolymer materials using terahertz time-domain spectroscopy*. 2009, Appl. Opt., pp. 2262-2266, modeled the presence of water in polymer via a linear model for the effective absorption coefficient α and the volume fraction of water X:

$$\alpha_{eff}(\omega) = (1-X)\alpha_h(\omega) + X\alpha_w(\omega) \qquad (2)$$

where eff stands for the effective medium, h stands for the host medium and w stands for the water. Other effective medium models include the Landu, Lifshitz, and Loyenga (LLL) model—derived in the limit of low dielectric contrast mixtures—in which the dielectric permittivity $\in$ is modeled as $$\sqrt[3]{\in_{eff}} = (1-X)\sqrt[3]{\in_h} + X\sqrt[3]{\in_w}. \qquad (3)$$

The complex dielectric permittivity is related to the real refractive index n and absorption coefficient α through $$\varepsilon = \varepsilon_r + i\varepsilon_i = \left[n^2 - \left(\frac{\alpha\lambda}{2\pi}\right)^2\right] - i\left[n\frac{\alpha\lambda}{\pi}\right] \qquad (4)$$

where n is the real index of refraction, λ is the vacuum wavelength of the radiation, and α is the absorption coefficient of the THz electric field (the absorption coefficient of power is 2α).

For multiple embodiments of the present invention, to determine the weight percentage of water in the cork and corresponding THz absorbance, the THz absorbance of the cork is modeled using Garnett effective medium theory. Garnett theory (See, Maxwell-Garnett, J C., *Colours in metal glasses and metallic films*. 1904, Phil. Trans. R. Soc. Lond. Ser. A, Vol. 206, pp. 385-420) calculates the effective dielectric properties of a material formed by the presence of small (spherical) particles embedded in a host material:

$$\frac{\varepsilon_{eff} - \varepsilon_h}{\varepsilon_{eff} + 2\varepsilon_h} = X \frac{\varepsilon_p - \varepsilon_h}{\varepsilon_p + 2\varepsilon_h} \qquad (5)$$

In the case of dry natural cork, the host material is that of the cell wall with the embedded particles being the cell lumen (ie. empty space inside of the cell walls). Typically, cork cells are 80-95% empty space.

The refractive index of cork is estimated to be 1.1 (Hor, Y. L., Federici, J. F. and Wample, R. L., *Non-destructive evaluation of cork enclosures using terahertz/millimeter wave spectroscopy and imaging*. 2008, Appl. Opt., Vol. 47, pp. 72-78) while the frequency dependent absorbance can be written as $$\alpha(v) = Cv^m + B \qquad (6)$$

where C=0.792, m=1.13, B=0.09 are typical values for spring growth cork cells which are 4.4 mm thick, and v is in units of THz.

Figure 8A:
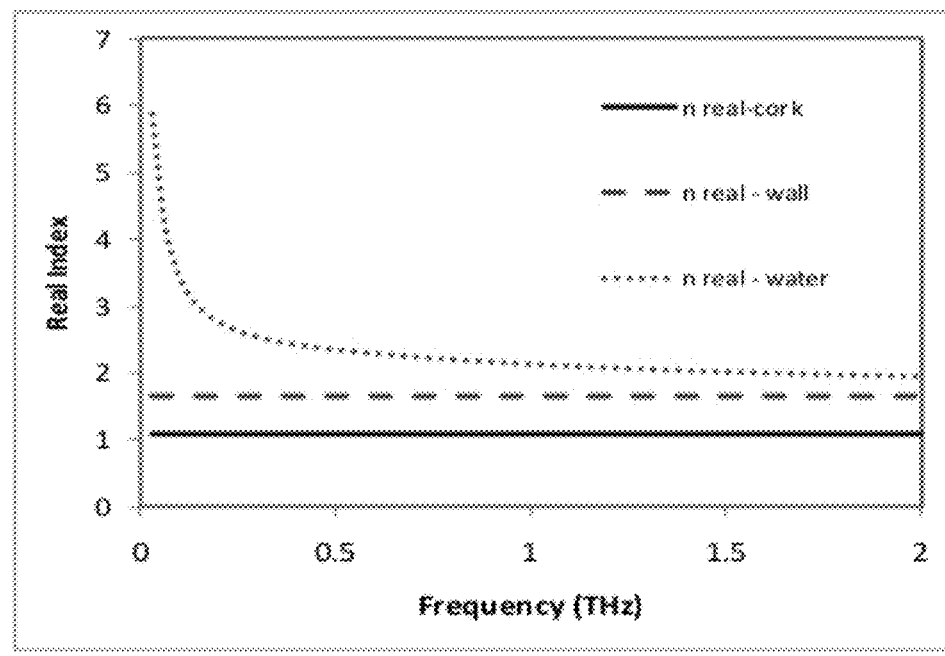
FIG. 8A graphically depicts frequency dependent real indices of refraction of natural cork (solid) from Eq. (6), unbounded water (dots) from the Debye model (See, Ronne, Cecilie, et al. *Investigation of the temperature dependence of dielectric relaxation in liquid water by THz reflection spectroscopy and molecular dynamics simulation.* 14, 1997, J. Chem. Phys, Vol. 107, pp. 5319-31), and calculated cork cell wall (dashed) from Eq. (5)
Figure 8B:
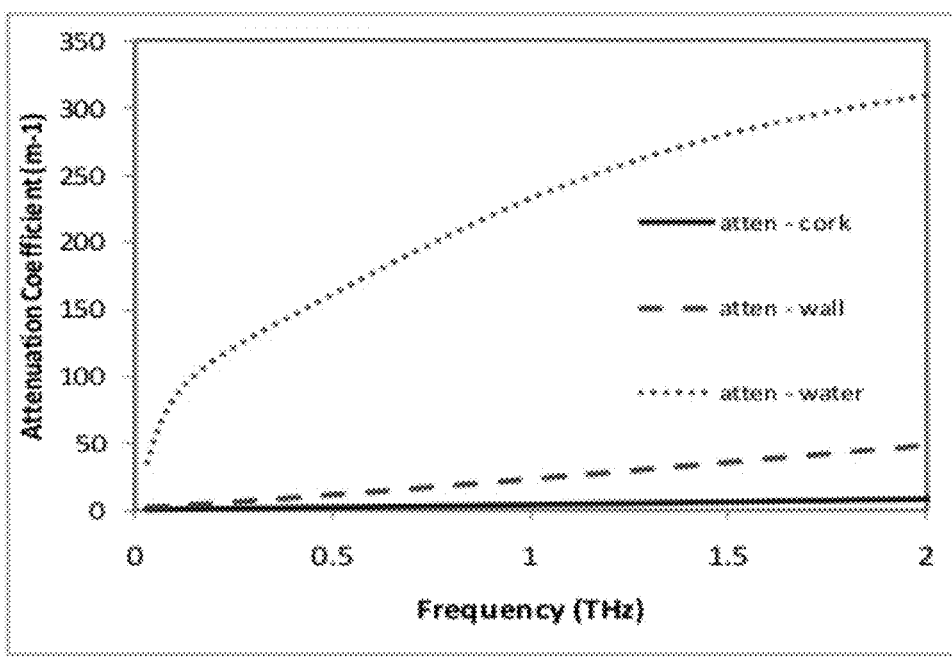
FIG. 8B graphically depicts corresponding attenuation coefficients.

Treating natural cork as an effective medium comprised of host material of cell walls with air "particles" intermixed in the host material, one can then determine the effective dielectric permittivity of cork (Eq. (4)) using n=1.1 and the absorption coefficient of Eq. (6) for multiple embodiments of the present invention. Using this effective permittivity, the dielectric constant of air ($\in_p=1$), and the assumption that the air "particles" comprise 85% of the cork cell volume, one can use Eq. (5) to estimate that the dielectric permittivity of the cork cell walls as shown in FIGS. 8A and 8B.

Figure 9:
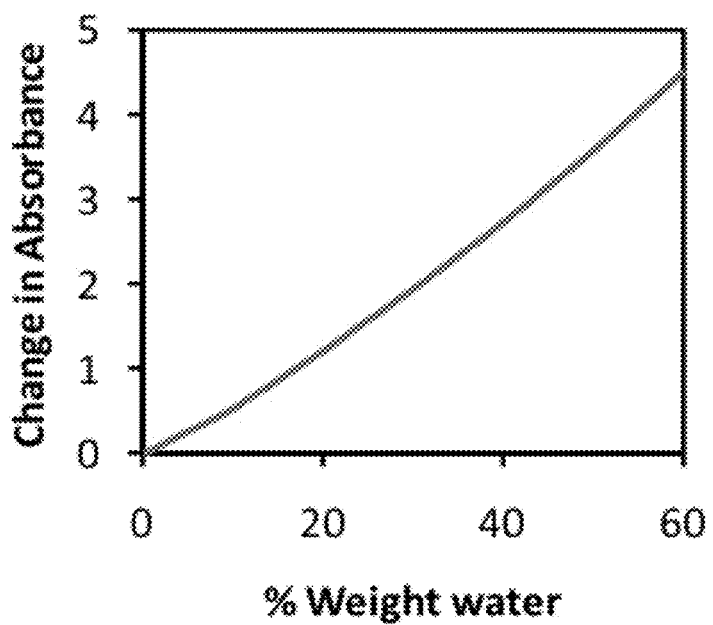
FIG. 9 graphically depicts calculated change in absorbance of wet cork relative to dry cork as a function of % weight of water relative to the weight of a dry cork in an embodiment wherein the thickness of the cork is 4 mm.

In one embodiment, from the calculated dielectric permittivity of the cork cell walls, one can estimate the effective dielectric permittivity of a water absorption by the cork cell walls by treating the dry cell wall dielectric permittivity (FIGS. 8A and 8B) as the "host" material and water as the "particles". The overall dielectric permittivity of wet natural cork then for said embodiment is calculated using a "host" material of wet cell walls embedded with "particles" of air. Based on these calculations, the net change in the absorbance of a 4.4 mm thick wet natural cork relative to dry natural cork as a function of water content is shown in FIG. 9. Note that the 60% by weight saturation threshold corresponds to an absorbance level of roughly 4.49.

Clearly, detailed modeling of the effective dielectric of natural cork is quite complicated. For example, the cork cell is not spherical (as is assumed in the MG model) but rather a Kelvin polyhedron. Pereira, H., *Cork: Biology, Production and Uses*. New York: Elsevier, 2007 ISBN-13: 978-0-444-52967-1. The Garnett theory is sufficient for multiple embodiments of the present invention since the Kelvin polyhedron more closely resembles a sphere than a long tube or flat disk. The LLL model—which is shape independent—only applies if the difference in the dielectric values of the host and particles is small. For wet cork cells, there is a large dielectric mismatch between the air of the cell lumens and the dielectric value of the water or cell wall. In addition, in one embodiment there is no differentiation between cell structure from spring or autumn growth of the cork oak tree. Furthermore, one embodiment does not explicitly take into account the presence of lenticels, cracks, or voids in calculating change in absorbance versus percent weight of water. Lastly, the small correction between bound water (water molecules bound to the sample material) and free liquid water is not included in certain embodiments of the present invention. Therefore, the change in absorbance versus percent weight of water as exemplified in FIG. 9 should be interpreted as an approximation used to predict the effective diffusion coefficient of the natural cork.

Figure 10:
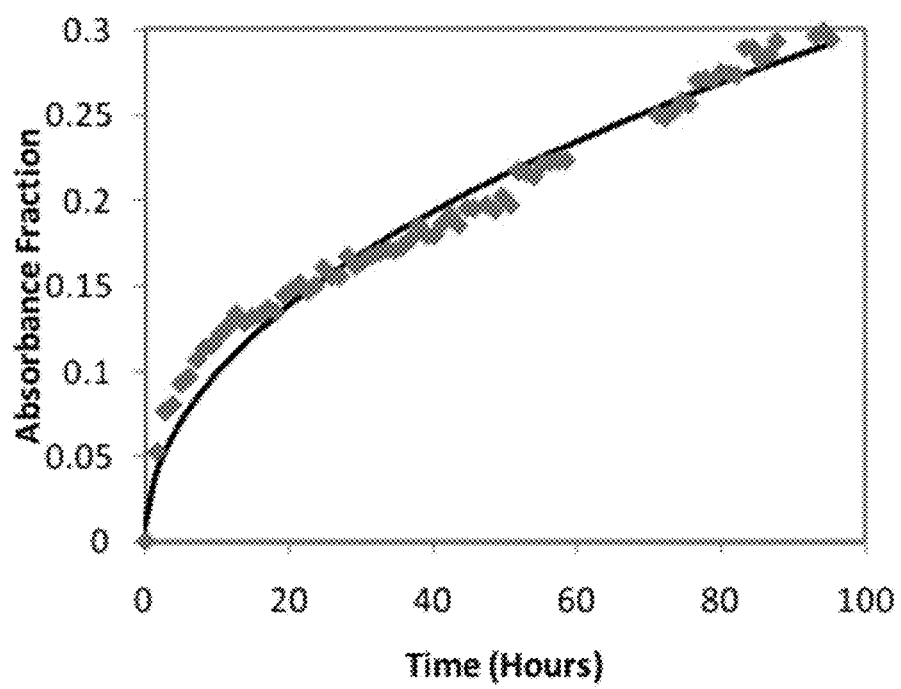
FIG. 10 graphically depicts Measured Absorbance fraction (relative to 4.49 Absorbance) versus time averaged over entire cork; the solid line is a best fit to the experimental data using Eq. (7) with a diffusion coefficient of $2.2 \times 10^{-4}$ cm$^2$/hr ($6.11 \times 10^{-12}$ m$^2$/s)

The extraction of a diffusion coefficient from experimental data is complicated by the fact that cork is not uniform. The non-uniformity arises from the presence of lenticular channels in the direction of radial tree growth as well as the presence of defects, cracks, and voids in the cork. In order to extract an effective diffusion coefficient for the entire cork disk to compare with previously published results for embodiments of the present invention the diffusion processes are modeled using the Fick equation for diffusion through an isotropic disk with a constant liquid concentration at its boundary:

$$\frac{M_t}{M_\infty} = 1 - \sum_{n=1}^{\infty} \frac{4}{a^2 \sigma_n^2} \cdot e^{-D\sigma_n^2(t-t_0)} \qquad (7)$$

$$\{\sigma_n \mid J_0(a \cdot \sigma_n) = 0\}$$

where $M_t$ and $M_\infty$ are the amount of diffusing water at time t and t=∞, respectively. See, Crank, J., *The Mathematics of Diffusion*. Clarendon: Oxford, 2001. For multiple embodiments of the present invention the cork disk has a radius a and an effective diffusion coefficient D. The variable $\sigma_n$ is the n-th root of the zero-th order Bessel function of the first kind. For certain exemplary embodiments, the assumption is made that the values of M can be represented by the average THz absorbance of the cork sample with $M_\infty=4.49$ corresponding to fully saturated (60%) cork cell walls. Using the data of FIG. 10, the ratio $M|M_\infty$, averaged over the entire cork versus time is calculated (FIG. 10). A best fit using Eq. (7) yields a diffusion coefficient of $6.1 \times 10^{-12}$ m$^2$/s. This value is comparable to the value determined by Rosa and Fortes using the cork immersion method. A similar analysis of the axial diffusion of FIG. 20 (discussed in further detail hereinbelow) yields an effective axial diffusion coefficient roughly a factor of 7 smaller than that calculated for the circular cross-section of cork. This result is qualitatively consistent with the immersion measurements of Rosa and Fortes who demonstrated that non-radial diffusion is roughly a factor of 4 smaller than radial diffusion.

Diffusion throughout the cork is not uniform as can be seen in FIGS. 17A-18H. The inhomogeneity of the cork (e.g due to cracks, voids, lenticular channels) implies that there are local variations in the diffusion coefficient. An analysis on multiple regions of the cork was performed to illustrate this point. FIG. 11C shows a composite visible image of the front and back surfaces of the cork sample and FIG. 12 shows the corresponding THz absorbance image of dry cork in the 0.65-0.7 THz range. The regions for localized analysis—labeled 0 to 9—are indicated in the THz image. Regions 1 and 2 correspond to large channels in the cork. Region 3 corresponds to a pristine region of cork which only absorbs water after a long time. Region 4 corresponds to a crescent shaped empty cavity in the cork which was intentionally created with a cork screw. Regions 5-8 correspond to grain structure in the cork. Regions 5 and 8 correspond to grains with enhanced THz absorbance compared to Regions 6 and 7. Regions 9 and 0 are adjacent locations near the edge of the cork. Region 0 is in a channel while Region 9 lies just outside of the channel.

Figure 13:
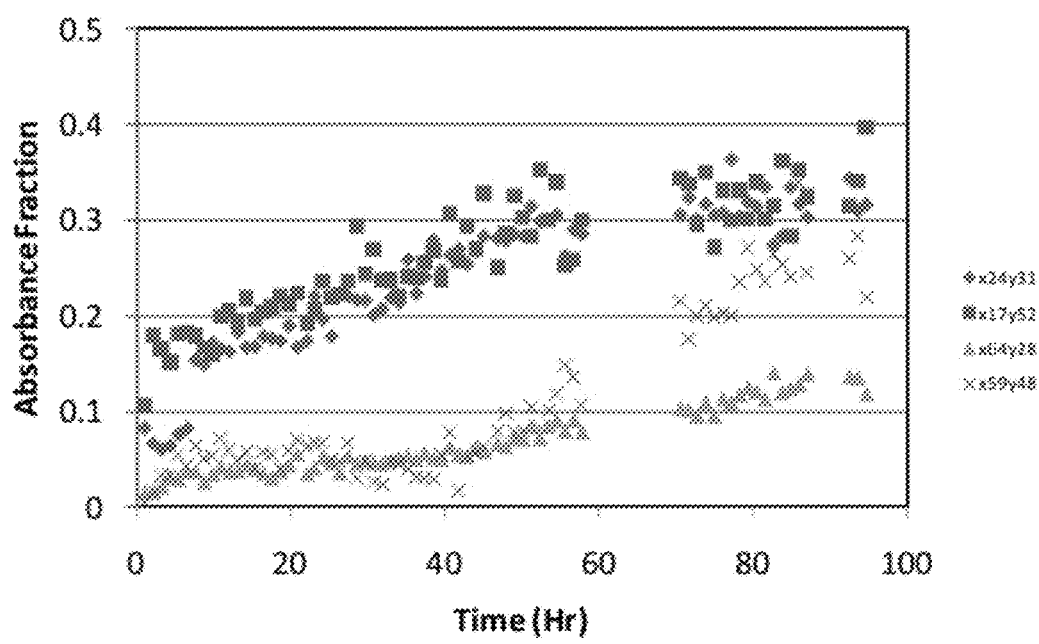
FIG. 13 graphically depicts absorbance fraction versus time for Regions 1 (diamond), 2 (square), 3 (triangle) and 4 (X) labeled in FIG. 12.

At each position in FIG. 12—analogous to the analysis which produced FIG. 11C—the average absorbance between 0.65-0.7 THz is calculated as a function of time. In one embodiment, in order to smooth the resulting absorbance data, values within one pixel of the center positions are averaged together. The dry cork absorbance value at that location is subtracted from the data for said embodiment. Lastly, for said embodiment, the data is normalized to the 60% saturated water value of 4.49. The corresponding absorbance fraction corresponds to the presence of water in the cork structure. The resulting curves for Regions 1-4 are plotted in FIG. 13.

In comparing Regions 1 and 2 which are located inside of channels, there is an initial rapid rise in the absorbance due to water in the first few hours. This is consistent with NMR observations that water quickly fills the lenticular channels of cork as well as observations by Fortes and Rosa that water is quickly absorbed by the boundaries of the cork. It is also interesting that there appears to be a "time delay" of ~7 hours in the onset of absorbance in Region 1 compared to Region 2. Without being confined to a single theory, this delay is attributed to the fact that Region 2 is closer to the surface of the cork while Region 1 is further in the interior of the channel and would require the water to travel a longer distance to reach the interior of the channel.

Region 4, which includes a cavity within the cork, shows interesting behavior. From 0-40 hours, there is a slow increase in the concentration of water. After ~45 hours, there is a rapid increase in the absorbance. As is shown in FIG. 19 (discussed further hereinbelow), at this time, water begins to noticeably fill in the crescent-shaped void in the cork. Therefore, it is reasonable to assume that prior to 40 hours, the water is predominately diffusing via cork cell walls into Region 4. After 40 hours, the cresent-shaped void begins to fill with water resulting in a large increase in THz absorbance. Region 3 corresponds to a region of cork which takes a long time to absorb water. Note that in Regions 3 and 4 the THz absorbance (and concentration of water) very gradually increases with time prior to 40 hours. However, since Region 3 is free of voids in the cork, there is not a dramatic increase in the absorbance after 40 hours as there is in Region 4.

Figure 14:
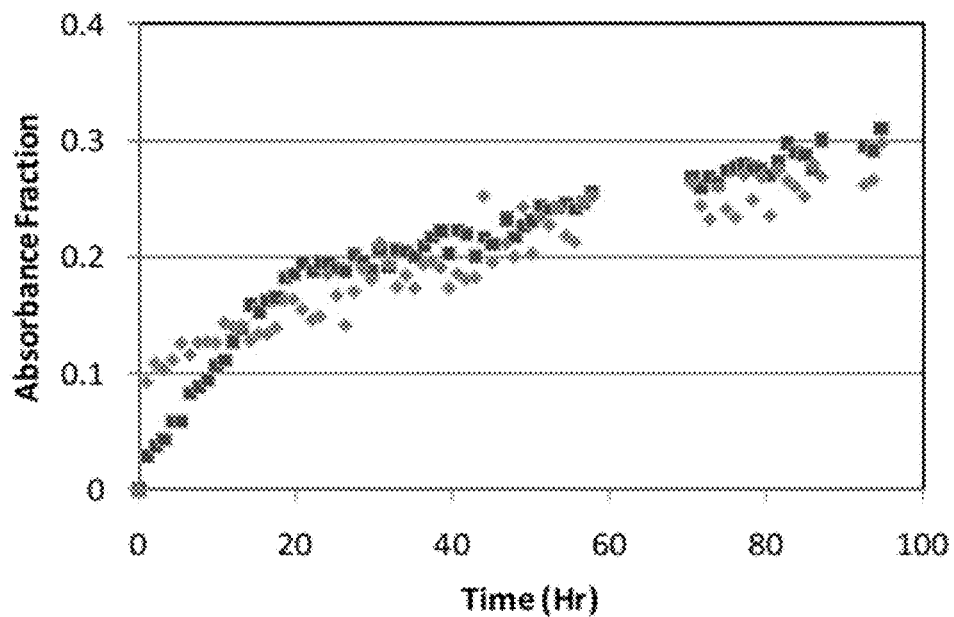
FIG. 14 graphically depicts absorbance fraction versus time for Region 0 (diamond) and 9 (square) labeled in FIG. 12.

A comparison of the normalized absorbance inside of a lenticular channel (Region 0) to a nearby location outside of the channel (Region 9) is shown in FIG. 14. As with Regions 1 and 2, there is an immediate increase in the absorbance due to the diffusion of water into these regions close to the cork's surface. However, Region 0 in the channel shows a larger absorbance and water concentration for t<10 hours. Since Regions 0 and 9 are located near each other, the presence of a large water concentration in Region 0 will induce a large flux of water flowing into Region 9. At t=20 hours, there is no longer a large gradient in the water concentration between the two regions resulting in commensurate concentrations of water in the two regions.

Figure 15:
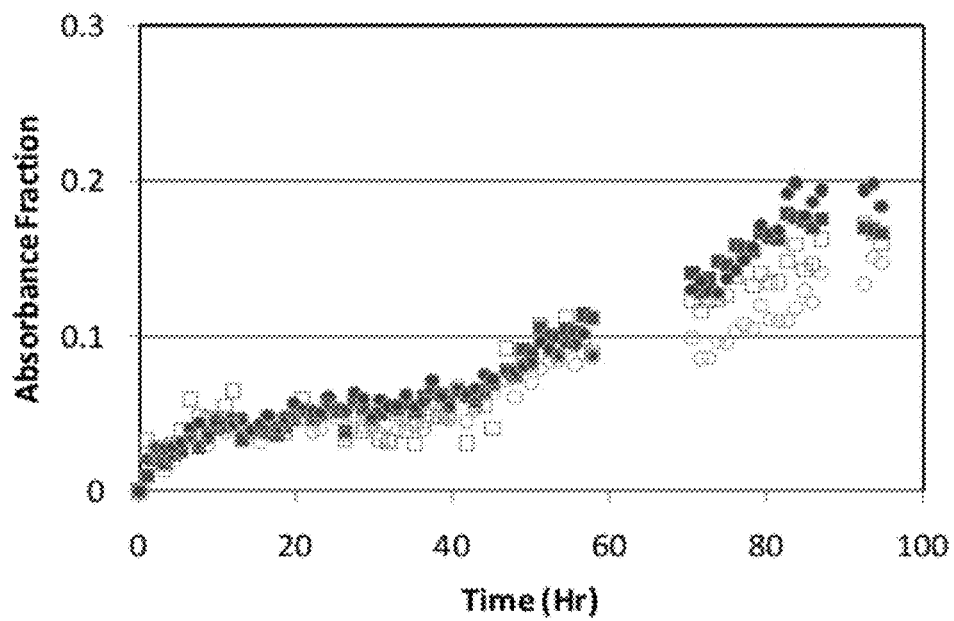
FIG. 15 graphically depicts absorbance fraction versus time for Region 5 (open square), 6 (solid square), 7 (solid circle) and 8 (open circle) labeled in FIG. 12.

Now referring to FIG. 15, the time evolution of the absorbance fraction of the grain structure in the cork is compared. Regions 5 and 6 correspond to "light" and "dark" grains near the middle of the cork sample while Regions 8 and 7 correspond to similar grains near the top of the cork structure. Note that all the grain locations behave essentially the same prior to t=40 hours. After 40 hours, there is a dramatic increase in the rate of water diffusion into these regions. As with FIG. 13, this sudden change is attributed to the filling of the crescent void near Region 4. The large concentration of water in the void creates a large gradient in the concentration of water relative to nearby regions essentially driving the diffusion of water into these regions. For time periods above 70 hours, there does appear to be a lower concentration of water in the "light" grains of the cork compared to the "dark" grains. While this observation is suggestive that there is a variation in the diffusion coefficient between autumn and spring growth grains in the cork, it is difficult to draw a definitive conclusion since the boundary conditions (i.e., the water concentration) surrounding the regions of interest are dynamic and not controlled during the experiment.

THz time-domain imaging is shown to be a viable non-destructive evaluation tool to measure the local and average diffusion of water in natural cork. In comparison, conventional methods of measuring liquid diffusion in natural cork typically average over the local variations in cork structure. From time-dependent THz images of water concentration, it is clear that lenticels, cracks and voids in the cork strongly influence the local as well as average diffusion properties. Localized measurements of water diffusion are in good agreement with previous observations: (a) channels near the surface quickly absorb water (b) diffusion in the radial growth direction is faster than the non-radial directions.

Exemplary Embodiments

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed.

Figure 16:
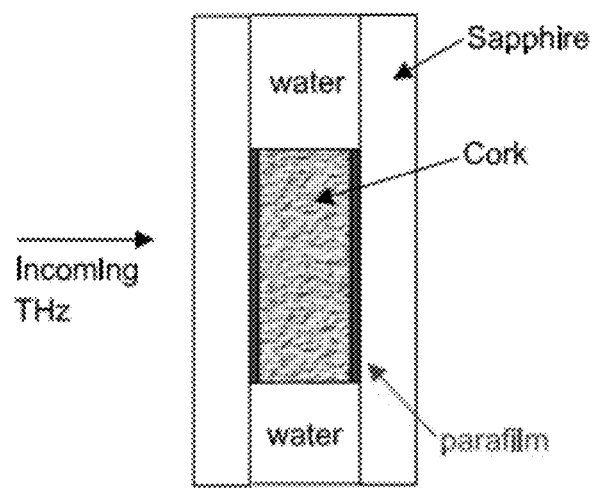
FIG. 16 is a schematic view of a sample enclosure in accordance with one embodiment of the present invention.
Figures 18A, 18B, 18C, 18D, 18E, 18F, 18G, 18H:
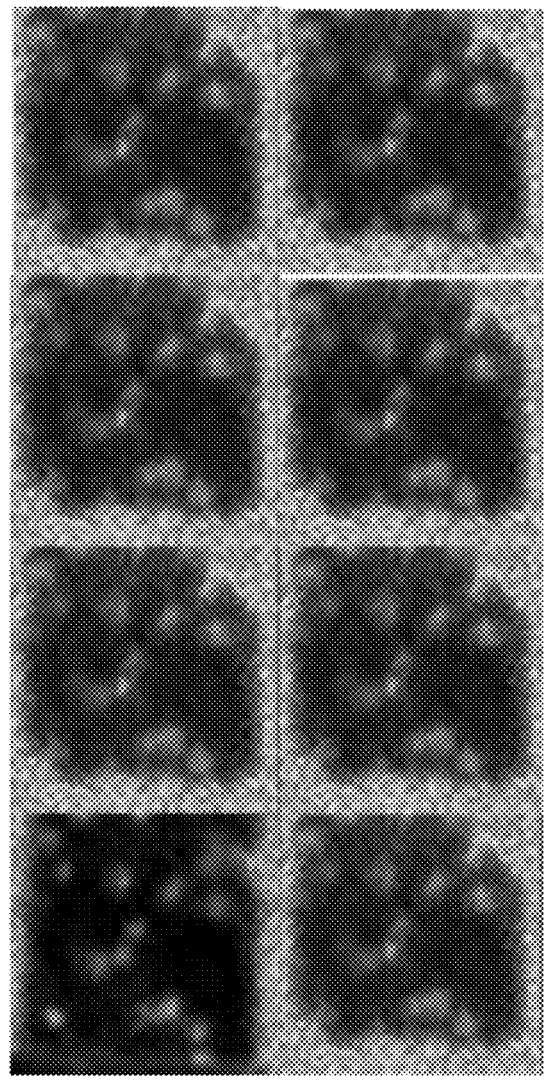
FIGS. 18A-18H graphically depict THz absorbance (0.65-0.7 THz) through cork cross-section at 0 hr (dry cork, FIG. 18A), 1.75 hr (FIG. 18B), 5.25 hr (FIG. 18C), 25.25 hr (FIG. 18D), 51.25 hr (FIG. 18E), 56.75 hr (FIG. 18F), 144 hr (FIG. 18G), and 316.5 hr (FIG. 18H), respectively; dark regions correspond to low absorbance while bright regions correspond to high absorbance; the lenticels are bright (corresponding to high attenuation) in the dry image due to efficient scattering of the THz radiation by the boundaries of the channel.

In accordance with one embodiment, natural cork samples were obtained from wine stoppers that had been dried in ambient air for several days. The samples were cut from the side that had not been in contact with the wine. Two types of samples were studied: circularly shaped samples cut parallel to the circular cross-section of the cork stopper and rectangularly shaped samples cut parallel to the long axis of the cork stopper. Natural cork stoppers are manufactured such that the long axis of the cork corresponds to the axial direction of cork tree growth whereas the circular cross-section includes both the radial grown direction and the tangential growth direction which is parallel to the grain in the cork. For this embodiment, typical circular samples had a radius and thickness of about 10.5 mm and about 4 mm, respectively. The axial samples had dimensions of about 16 mm parallel to the axial direction, about 14 mm width and a thickness of about 5 mm. Now referring to FIG. 16, for measurements of diffusion in the circular cross-section, the cork sample was enclosed between two sapphire windows using parafilm to only allow water absorption along the circumference of the sample. The sapphire windows/cork sample was encased in heat-shrink tubing to make a waterproof enclosure. Distilled water was injected into the enclosure to keep the cork submerged. For diffusion measurements along the long axis of the cork, a similar approach was taken to prepare the sample. In addition to the parafilm to prevent water penetration into the cork along the sapphire window surface, the surface of the cork was sealed using a waterproof glue to prevent any water entry through the cork surface perpendicular to the axial direction.

For one exemplary embodiment of the present invention, terahertz spectral images were acquired using the Picometrix T-Ray 2000 system as described in Hor, Y. L., Federici, J. F. and Wample, R. L., *Non-destructive evaluation of cork enclosures using terahertz/millimeter wave spectroscopy and imaging.* 2008, Appl. Opt., Vol. 47, pp. 72-78. Acquisition of a THz image of the sample required approximately 1 hour. In one exemplary embodiment an image of the dry cork sample was first recorded. Subsequent to the injection of water into the sample holder, THz images were recorded continuously every hour. Prior to the acquisition of each THz image, the cork sample was translated out of the THz beam path and a background time-domain scan was recorded. The pixel size of the images was typically about 0.5 mm.

For each pixel in the image, the THz frequency dependent absorbance was calculated as:

$$A(\omega) = -\ln(T(\omega)) = -\ln(|E_s(\omega)|/|E_r(\omega)|) \qquad (8)$$

where $|E_r(\omega)|$ and $|E_s(\omega)|$ are the magnitudes of the reference and sample THz electric fields as calculated by the Fourier transform of the time-domain data, and $T(\omega)$ is the transmission through the sample. To obtain a single value at each pixel position and construct an image, the absorbance is averaged over a narrow bandwidth for said embodiment.

The optimal bandwidth for image processing is determined by two factors: spatial resolution and signal-to-noise. Since the higher frequencies of THz radiation can be focused to smaller spot sizes due to diffractive effects, better spatial resolution is generally realized in the THz images as the THz frequency increases. However, the signal-to-noise ratio drops dramatically as the THz frequency increases. Consequently, there is a trade-off between spatial resolution and signal-to-noise. To determine an effective compromise, the THz spectra in a region of cork after ~95 hours of soaking are examined. The noise limit of one embodiment is determined by placing a metal plate in front of the THz detector during a time-domain scan. This scan represents the noise limit of the system when no THz radiation reaches the detector. The range from about 0.65-0.70 THz was chosen as the spectral bandwidth for data processing; the THz frequency is high enough to provide good spatial resolution (~0.5 mm) with adequate signal-to-noise for said embodiment, however alternate embodiments embrace alternate ranges.

In one embodiment, once the cork absorbance images are created for each time interval, the images are stitched together to create a time-lapsed movie that shows the diffusion of water through the corks. A small Gaussian filter and stabilization algorithm (K. Li, "The image stabilizer plugin for ImageJ," http://www.cs.cmu.edu/~kangli/code/Image_Stabilizer.html, February, 2008. [Online]) is applied to the images to smooth the spatial noise.

Montages of the resulting movies for both the circular cross-section and axial cork samples are shown in FIGS. 17A-H and 18A-H, respectively for said embodiment. The area surrounding the cork initially has low absorbance. After the introduction of water, this area becomes highly absorbing. The cork sample in FIGS. 17A-H is oriented so that the radial direction of cork growth is parallel to the bottom of the page. The tangential growth direction is perpendicular to the bottom of the page. While the cork sample is circularly shaped, the diffusion of water does not exhibit radial symmetry due to the varying diffusion rates in the different growth directions. Clearly, the diffusion of water is more rapid in the radial direction of tree growth compared to the tangential direction. It is also clear in comparing FIG. 11C and FIGS. 17A-H that the lenticels and cracks/voids quickly fill with water therefore dominating the diffusion of water. This behavior is consistent with previous water diffusion measurements using NMR. In contrast, the cork sample of FIGS. 18A-H is oriented so that the axial growth direction is parallel to the bottom of the page while the radial growth direction is perpendicular to the page. In the dry cork image, the lenticels appear as bright spots in the interior of the cork due to significant scattering of THz radiation by the edges of the lenticular channels. Once water is added to the sample chamber, the diffusion in the axial growth direction is comparatively much slower than the diffusion shown in FIGS. 17A-H.

In one exemplary embodiment, in order to create images which only show the flow of water through the cork, the dry cork images are subtracted from the data of FIGS. 17A-H and FIGS. 18A-H thereby removing the absorbance due to the dry cork features and only leaving the absorbance of the water inside the cork. The movie montages for the radial and axial water-only diffusion are shown in FIGS. 19A-H and 20A-H, respectively. Clearly the water diffuses much more rapidly in the radial growth direction compared to the axial growth direction of the cork.

Previous THz measurements of solvent diffusion in polymers used a reflection geometry to track the wave-front of the diffusion. Obradovic, J., et al., *The use of THz time-domain reflection measurements to investigate solvent difusion in polymers.* 2007, Polymer, Vol. 48, pp. 3494-3503. In the transmission configuration of the present invention, the location of the wavefront may be extracted by processing the images of FIGS. 19A-H and 20A-H to monitor which pixels exhibit an absorbance value above a fixed threshold. The THz absorbance value can be related to the concentration of water in the cork. The images are segmented into binary images with an absorbance threshold of 0.5 (corresponding to 9.2% by weight water) for FIGS. 19A-H and an absorbance threshold of 0.3 (6.8% by weight water) for FIG. 20A-H as shown in FIGS. 21A-H and 22A-H, respectively. As can be seen from FIGS. 21B-H, water diffusion in the radial growth direction is much faster than along the tangential direction. This is consistent with cork submersion studies. Rosa, M. E. and Fortes, M. A., *Water Absroption by Cork.* 4, 1993, Wood and Fiber Science, Vol. 25, pp. 339-348. Rosa and Fortes attribute this effect to the alignment of the cell wall which allows more flow in the radial direction as well as the presence of lenticular channels aligned in the radial direction, which will contribute to faster diffusion. Rosa and Fortes, ibid. As can be seen in FIGS. 22B-H, the rapid diffusion of water in the lenticular channels is mitigated since the predominate flow of water is in the axial direction: even though the channels can quickly fill with water, they are spatially isolated from each other in the axial direction resulting in a lower average diffusion coefficient compared to FIGS. 21B-H.

THz imaging as a non-contact/non-destructive method enables real-time measurements of liquid diffusion in a variety of configurations. For example, in one embodiment, it is used to measure diffusion of wine into a cork stopper in the neck of a wine bottle. In further embodiments it may be used as a technique to study the effect of cork structure on the extraction and migration of non-volatile chemicals, such as TCA, from the cork.

Based on the foregoing it is apparent THz imaging employing the present methods and apparatus for sample evaluation is superior to visual inspection by human experts and camera systems, which can only inspect the surface of a sample such as a cork. THz imaging enables evaluation of the internal structure of the cork as well as the surface structure. For example, the spatial resolution of the camera system reported in J. Chang, et al., "Cork quality classification system using a unified image processing and fuzzy-neural network methodology," IEEE Trans Neural Networks 8, 964-974 (1997) images the end of a cork with approximately 90 by 90 pixels. The THz images of the end of the cork are roughly 45 by 45 pixels corresponding to 0.5 mm spatial resolution. The maximum resolution is determined by the step size of each pixel as well as the THz frequency. Since the spatial resolution of a free-space optical system is typically limited by diffractive effects to be on the order of the wavelength of light, one would expect that the resolution limit of 1 THz radiation would be on the order of 300 μm. Therefore, halving the pixel step size to 250 μm in the THz images would give approximately the same spatial resolution as the visible images of the aforementioned camera system but with the added advantage of probing the interior structure of the cork.

By way of further comparison, as described in A. Brunetti et al., "Cork quality estimation by using Compton tomography," Nuclear Instruments and Methods in Physics Research Section B: Beam Interactions with Materials and Atoms 196, 161-168 (2002), an x-ray transmission geometry does not produce good contrast x-ray images. The poor contrast results from the fact that the interaction between the x-rays and cork is very weak so that there is very little loss of x-ray power in going through the natural cork cells and the voids. This is in contrast with the THz transmission imaging methods and apparatus of the present invention which provides for a strong interaction between the THz radiation and the cork cell structure due to Mie scattering: the size of the cork cells is comparable to the wavelength of the probing radiation. THz radiation, as compared to x-rays, is more efficiently scattered by the cells and voids indicating that THz imaging is a much more sensitive method for imaging the internal structure of the cork. The x-ray tomography technique described in Brunetti et al. measures scattered x-rays by placing the x-ray receiver approximately perpendicular to the incoming direction of the probing x-rays. Regions of high electron density more efficiently scatter the x-rays resulting in contrast between the cork and voids. The x-ray beam is collimated to a diameter of roughly 1 mm and passed through the sample. Since the spatial resolution of the x-ray method is limited to roughly 1 mm (as determined by the diameter of the probing x-ray beam), the spatial resolution of the THz system is inherently superior to the x-ray method described in Brunetti et al. Moreover, a two-dimensional linear scan as well as a rotational scan is required to reconstruct the x-ray tomography images. Since THz radiation interacts much more strongly with the cork cell structure through Mie scattering, a simple transmission image requires only a 2-D linear scan.

The present methods are superior to nuclear magnetic resonance (NMR) microscopy. NMR microscopy used to image the diffusion of water into natural cork yielded results suggesting that after three days, the absorption of water is limited to the lenticels of the cork, wherein the lenticular channels had diameters between 1.0-1.5 mm. Gil, A. M., et al., *An NMR microscopy study of water absorption in cork.* 2000, J. Materials Sci., Vol. 35, pp. 1891-1900.

Moreover, the present methods and apparatus may be used to distinguish between mature cork and green cork (higher concentration of water or cytoplasmic liquid). Since water and liquids in general highly reflect THz radiation, green cork will efficiently reflect/attenuate THz radiation compared to mature cork.

The presently described methods have various applications. One embodiment of the application is to identify whether a particular sealed container such as a wine bottle with a natural cork seal is likely to have cork taint. Other embodiments of the application include identification of contamination or spoilage of other products, including but not limited to oils, such as pressed extra virgin olive oil that is bottled and sealed with a natural cork, or vinegar. Other embodiments include identifying that proper fermentation of, by way of example only, beer, mead, sauerkraut or kim chi, or aging of food products such as cheese has occurred. These examples are merely illustrative of possible additional applications of the presently described method and can be in no way construed as a limitation of the use thereof.

Applicants have attempted to disclose all embodiments and applications of the described subject matter that could be reasonably foreseen. However, there may be unforeseeable, insubstantial modifications that remain as equivalents. While the present invention has been described in conjunction with specific, exemplary embodiments thereof, it is evident that many alterations, modifications, and variations will be apparent to those skilled in the art in light of the foregoing description without departing from the spirit or scope of the present disclosure. Accordingly, the present disclosure is intended to embrace all such alterations, modifications, and variations of the above detailed description.

All references cited herein are incorporated fully by reference. The following references are also hereby incorporated fully by reference:

T. Chang, G. Han, J. M. Valverde, N. C. Griswold, J. F. Duque-Carrillo, and E. S anchez-Sinencio, "Cork quality classification system using a unified image processing and fuzzy-neural network methodology," IEEE Trans Neural Networks 8, 964-974 (1997).

R. Juanola, D. Subirà, V. Salvadó, J. A. Garcia Regueiro and E. Anticó, "Evaluation of an extraction method in the determination of the 2,4,6-trichloroanisole content of tainted cork," J. Chromatography A 953, 207-14 (2002).

E. Lizarraga, Á. Irigoyen, V. Belsue and E. González-Peñas, "Determination of chloroanisole compounds in red wine by headspace solid-phase microextraction and gas chromatography—mass spectrometry," J. Chromatography A 1052, 145-9 (2004).

E. Herve, S. Price, G. Burns, P. Weber, presented at the ASEV Annual Meeting, Reno, Nev., 2 Jul. 1999. http://www-.corkqc.com/asev/asev2-2.htm.

A. Brunetti, R. Cesareo, B. Golosio, P. Luciano and A. Ruggero, "Cork quality estimation by using Compton tomography," Nuclear Instruments and Methods in Physics Research Section B: Beam Interactions with Materials and Atoms 196, 161-168 (2002).

D. Zimdars, J. S. White, G. Stuk, A. Chemovsky, G. Fichter, and S. Williamson, "Large area terahertz imaging and non-destructive evaluation applications," Insight-Non-Destructive Testing and Condition Monitoring 48, 537-539 (2006).

D. Zimdars, J. A. Valdmanis, J. S. White, G. Stuk, W. P. Winfree, and E. I. Madaras, "Time domain terahertz detection of flaws within space shuttle sprayed on foam insulation" in *Conference on Lasers and Electro-Optics/Quantum Electronics and Laser Science and Photonic Applications Systems Technologies*, Technical Digest (CD) (Optical Society of America, 2004), paper CThN4. http://www.opticsinfobase.org/abstract.cfm?id=104293.

H. S. Chua, P. C. Upadhya, A. D. Haigh, J. Obradovic, A. A. P. Gibson, and E. H. Linfield, "Terahertz time-domain spectroscopy of wheat grain" in *Conference Digest of the 2004 Joint 29th International Conference on Infrared and Millimeter Waves and 12th International Conference on Terahertz Electronics* (Institute of Electrical and Electronics Engineers, New York, 2004), pp 399-400; H. S. Chua, J. Obradovic, A. D. Haigh, P. C. Upadhya, O. Hirsch, D. Crawley, A. A. P. Gibson, and E. H. Linfield, "Terahertz time-domain spectroscopy of crushed wheat grain" in 2005 *IEEE MTT-S International Microwave Symposium* (Institute of Electrical and Electronics Engineers, New York, 2005), p 4.

S. Hadjiloucas, L. S. Karatzas, and J. W. Bowen, "Measurements of leaf water content using terahertz radiation," IEEE Trans. Microwave Theory and Techniques 47, 142-149 (1999); S. Hadjiloucas, R. K. H. Galvao, J. W. J. Bowen, "Analysis of spectroscopic measurements of leaf water content at terahertz frequencies using linear transforms", Opt. Soc. Am. A 19, 2495-2509 (2002).

M. Reid and R. Fedosejevs, "Terahertz birefringence and attenuation properties of wood and paper," Applied Optics 45, 2766-2772 (2006).

C. J. Strachan, T. Rades, D. A. Newnham, K. C. Gordon, M. Pepper, and P. F. Taday, "Using terahertz pulsed spectroscopy to study crystallinity of pharmaceutical materials," Chem. Phys. Lett. 390, 20-24 (2004).

D. S. Venables and C. A. Schmuttenmaer, "Spectroscopy and dynamics of mixtures of water with acetone, acetonitrile, and methanol," J. Chem. Phys. 113, 11222-36 (2000).

J. F. Federici, B. Schulkin, F. Huang, D. Gary, R. Barat, F. Oliveira, and D. Zimdars, "THz imaging and sensing for security applications-explosives, weapons and drugs," Semicond. Sci. Technol. 20, S266-80 (2005).

J. F. Federici, D. Gary, R. Barat, Z.-H. Michalopoulou, 'Detection of Explosives by Terahertz Imaging', in *Counter-Terrorism Detection Techniques of Explosives* Jehuda Yinon Ed. (Elsevier, 2007).

F. C. Delucia, "Spectroscopy in the Terahertz Spectral Region", in *Sensing with Terahertz Radiation*, D. Mittleman Ed. (Springer, 2003).

M. C. Beard, G. M. Turner, and C. A. Schmuttenmaer, "THz Spectroscopy," J. Phys. Chem B106, 7146-7159 (2002).

F. Huang, B. Schulkin, H. Altan, J. Federici, D. Gary, R. Barat, D. Zimdars, M. Chen and D. Tanner, "Terahertz study of 1,3,5-trinitro-s-triazine by time-domain and Fourier transform infrared spectroscopy," Appl. Phys. Lett, 85, 5535-7 (2004).

A. Nystrom, A. Grimvall, C. Krantz-Rulcker, R. Savenhed, K. Akerstrand, "water off-flavour caused by 2,4,6-trichloro-anisole," Water Science and Technology 25, 241-49 (1992).

S. Karlsson, S. Kaugare, A. Grimvall, H. Boren, R. Savenhed, "Formation of 2,4,6-trichlorophenol and 2,4,6-trichloro-anisole during treatment and distribution of drinking water," Water Science and Technology 31, 99-103 (1995).

A. Miki, A. Isogai, H. Utsunomiya, H. Iwata, "Identification of 2,4,6-trichloroanisole (TCA) causing a musty/muddy off-flavor in sake and its production in rice koji and moromi mash," J. Bioscience and Bioengineering 100, 178-83 (2005).

L. H. Aung, J. L. Smilanick, P. V. Vail, P. L. Hartsell, E. Gomez, "Investigations into the Origin of Chloroanisoles Causing Musty Off-Flavor of Raisins," J. Agricultural and Food Chemistry 44, 3294-96 (1996).

C. Silva Pereira, J. J. Figueiredo Marques, M. V. San Romao, "Cork taint in wine: Scientific knowledge and public perception—A critical review," Critical Reviews in Microbiology 26, 147-62 (2000).

A. P. Pollnitz, K. H. Pardon, D. Liacopoulos, G. K. Skouroumounis, M. A. Sefton, "The analysis of 2,4,6-trichloroanisole and other chloroanisoles in tainted wines and corks," Australian J. Grape and Wine Research 2, 184-90 (1996).

J. Gunschera, F. Fuhrmann, T. Salthammer, A. Schulze, E. Uhde, "Formation and emission of chloroanisoles as indoor pollutants," Environmental Science and Pollution Research 11, 147-51 (2004).

J. Prescott, L. Norris, M. Kunst, S. Kim, "Estimating a 'consumer rejection threshold' for cork taint in white wine," Food Quality and Preference 16, 345-49 (2005).

D. Mittleman, "Terahertz Imaging" in *Sensing with Terahertz Radiation*, D. Mittleman Ed. (Springer, 2003).

D. M. Mittleman, S. Hunsche, L. Boivin, M. C. Nuss, "T-ray tomography," Optics Letters 22, 904-6 (1997).

T. Yasui, T. Yasuda, T. Araki, E. Abraham, "Real-time two-dimensional terahertz tomography of moving objects," Optics Comm. 267, 128-36 (2006).

H. Zhong, J. Xu, X. Xie, T. Yuan, R. Reightler, E. Madaras, and X.-C. Zhang, "Nondestructive defect identification with terahertz time-of-flight tomography," IEEE Sensors Journal 5, 203-8 (2005).

What is claimed is:

1. A method of nondestructively measuring the diffusion of liquid in a material using THz time-domain imaging of at least a portion of the interior of the material comprising performing the steps of:

introducing THz radiation to a dry material;
receiving the THz radiation transmitted through the dry material;
collecting spectral data comprising absorbance values of the received THz radiation comprising acquiring an image one pixel at a time and recording the spectrum of THz radiation at each pixel while generating a THz image of at least a portion of the interior of the dry material;
recording the image of the dry material;
subsequently, injecting liquid into the dry material;
introducing THz radiation to the liquid-injected material;
receiving the THz radiation transmitted through the liquid-injected material;
collecting spectral data comprising absorbance values of the received THz radiation transmitted through the liquid-injected material comprising acquiring an image one pixel at a time and recording the spectrum of THz radiation at each pixel while generating a THz image of at least a portion of the interior of the liquid-injected material;
recording a THz image of the liquid-injected material at selected intervals, and
subtracting an absorbance value of the dry material from an absorbance value of the liquid-injected material to show diffusion of liquid in the liquid-injected material.

2. The method according to claim 1 comprising translating the material out of a path of the THz radiation and recording a background time-domain scan to obtain a reference prior to the acquisition of each THz image.

3. The method according to claim 1, comprising calculating the THz frequency dependent absorbance for each pixel in the image as $$A(\omega)=-\ln(T(\omega))=-\ln(|E_s(\omega)|/|E_r(\omega)|)$$

where $|E_r(\omega)|$ and $|E_s(\omega)|$ are the magnitudes of THz electric fields as calculated by the Fourier transform of the time-domain data of the reference and material, and $T(\omega)$ is the transmission through the material.

4. The method according to claim 3 comprising averaging the absorbance over a specified bandwidth range to obtain a single value at each pixel position and construct an image.

5. The method according to claim 4 wherein the specified bandwidth for image processing is 0.65-0.70 THz.

6. The method according to claim 1 comprising stitching together the recorded images to create a time-lapse movie that shows the diffusion of liquid through the material.

7. The method according to claim 6 comprising subtracting images of the material that are images of liquid-injected material.

8. The method according to claim 1 comprising applying a Gaussian filter and stabilization algorithm to the images to smooth spatial noise.

9. The method according to claim 1 wherein the material is cork.

10. The method according to claim 1 wherein the liquid is water.

11. The method according to claim 1 comprising, after injecting liquid into the material and recording a THz image of the liquid-injected material at selected intervals, extracting a location of a wavefront by processing images to monitor which pixels exhibit an absorbance value above a fixed threshold.

12. A method of nondestructively measuring the diffusion of liquid in a material using THz time-domain imaging of at least a portion of the interior of the material comprising:

introducing THz radiation to a dry material;
receiving the THz radiation transmitted through the dry material;
collecting spectral data comprising absorbance values of the received THz radiation comprising acquiring an image one pixel at a time and recording the spectrum of THz radiation at each pixel while generating a THz image of at least a portion of the interior of the dry material;
recording the image of the dry material;
subsequently, injecting liquid into the dry material;
introducing THz radiation to the liquid-injected material;
receiving the THz radiation transmitted through the liquid-injected material;

collecting spectral data comprising absorbance values of the received THz radiation transmitted through the liquid-injected material comprising acquiring an image one pixel at a time and recording the spectrum of THz radiation at each pixel while generating a THz image of at least a portion of the interior of the liquid-injected material;

recording a THz image of the liquid-injected material at selected intervals;

stitching together the recorded images to create a time-lapse movie that shows the diffusion of liquid through the material; and subtracting an absorbance value of the dry material from an absorbance value of the liquid-injected material to show diffusion of liquid in the liquid-injected material.

* * * * *